United States Patent
Tatake et al.

(10) Patent No.: US 6,525,184 B1
(45) Date of Patent: *Feb. 25, 2003

(54) SELF-REGULATED APOPTOSIS OF INFLAMMATORY CELLS

(75) Inventors: Revati J. Tatake, Sandy Hook, CT (US); Steven D. Marlin, Sandy Hook, CT (US); Randall W. Barton, Farmington, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/032,297

(22) Filed: Feb. 27, 1998

Related U.S. Application Data

(60) Provisional application No. 60/039,266, filed on Feb. 28, 1997.

(51) Int. Cl.[7] .......................... C07H 21/04; C12N 15/00; C12N 15/63; A61K 48/00
(52) U.S. Cl. ..................... 536/23.1; 536/23.2; 536/23.4; 536/24.1; 435/375; 435/320.1; 514/44
(58) Field of Search .......................... 514/44; 435/320.1, 435/375; 536/23.1, 23.2, 23.4, 24.1

(56) References Cited

U.S. PATENT DOCUMENTS

| | | |
|---|---|---|
| 5,744,304 A | 4/1998 | Munford |
| 5,792,751 A | 8/1998 | Ledley et al. |
| 6,004,942 A * | 12/1999 | Firestein et al. ............... 514/44 |

OTHER PUBLICATIONS

Rhoades, et al. The Journal of Biol. Chemistry. vol. 267, No. 31, pp. 22102–22107, Nov. 1992.*

Leitman, DC, et al; Identification of a Tumor Necrosis Factor–responsive Element in the Tumor Necrosis Facotr a Gene; The Journal of Biological Chemistry, 1991; 266(15) 9343:9346.

Chinnaiyan, A.M., et al., *Cell 81*:505–512 (1995).

Faucheu, C., et al., *EMBO J. 14*: 1914–1922 (1995).

Faucheu, C., et al., *Eur. J. Biochem. 236*: 207–213 (1996).

Miura, M., et al., *Cell 75*: 653–660 (1993).

Muzio, M., et al., *Cell 85*: 817–827 (1996).

Takashiba, S., et al., *Gene 131*: 307–308 (1993).

* cited by examiner

*Primary Examiner*—David Guzo
*Assistant Examiner*—Gerald G. Leffers, Jr.
(74) *Attorney, Agent, or Firm*—Robert P. Raymond; Susan K. Pöcchiari; Mary-Ellen M. Devlin

(57) ABSTRACT

This invention relates to the therapeutic induction of apoptosis in activated inflammatory cells, or cells at a site of inflammation, by introducing into those cells a chimeric gene containing an apoptosis-inducing gene (AIG) driven by a promoter of an inducible gene activated in inflammation and a promoter enhancer such that the inflammatory cells are targeted. In one embodiment, the chimeric gene comprises at least one TNFα promoter enhancer attached to a functional copy of a minimal TNFα promoter and further attached to at least one copy of an apoptosis-inducing gene, wherein expression of the gene is driven by the TNFα promoter. Attachment can be direct, distal, proximal or combinations thereof. Example apoptosis-inducing genes include caspase 3, caspase 4, caspase 5, Granzyme B. Advantageously, the TNFp-AIG chimeric gene is expressed in only those cells producing the inflammatory cytokine, TNFα. In addition, the TNFp-AIG chimeric gene also sequesters inducible TNFp transcription factors, thereby reducing endogenous production of TNFα. The invention also relates to methods of making and using self-regulated apoptosis chimeric genes and pharmaceutical compositions containing them for treating inflammatory diseases.

4 Claims, 14 Drawing Sheets pGL3 basic vector elements

5' SstI.XhoI.(-120/-706/-1005 to TSS.BglII).HindIII 3'

SEQUENCE LISTING

```
(1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 1178
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: reference human TNFa promoter (x) PUBLICATION INFORMATION:
        (A) AUTHORS: Takashiba, S., et al.
        (C) JOURNAL: Gene
        (D) VOLUME: 131
        (F) PAGES:   307-308

(xi) SEQUENCE DESCRIPTION: SEQ ID NO: 1:

GGGGAAGCAA AGGAGAAGCT GAGAAGATGA AGGAAAAGTC AGGGTCTGGA            50

GGGGCGGGGG TCAGGGAGCT CCTGGGAGAT ATGGCCACAT GTAGCGGCTC           100

TGAGGAATGG GTTACAGGAG ACCTCTGGGG AGATGTGACC ACAGCAATGG           150
```

-continued

```
GTAGGAGAAT GTCCAGGGCT ATGGAAGTCG AGTATCGGGG ACCCCCCCTT         200

AACGAAGACA GGGCCATGTA GAGGGCCCCA GGGAGTGAAA GAGCCTCCAG         250

GACCTCCAGG TATGGAATAC AGGGGACGTT TAAGAAGATA TGGCCACACA         300

CTGGGGCCCT GAGAAGTGAG AGCTTCATGA AAAAAATCAG GGACCCCAGA         350

GTTCCTTGGA AGCCAAGACT GAAACCAGCA TTATGAGTCT CCGGGTCAGA         400

ATGAAAGAAG AAGGCCTGCC CCAGTGGTCT GTGAATTCCC GGGGGTGATT         450

TCACTCCCCG GGCTGTCCCA GGCTTGTCCC TGCTACCCCC ACCCAGCCTT         500

TCCTGAGGCC TCAAGCTGCC ACCAAGCCCC CAGCTCCTTC TCCCCGCAGA         550

CCCAAACACA GGCCTCAGGA CTCAACACAG CTTTTCCCTC CAACCCCGTT         600

TTCTCTCCCT CAAGGACTCA GCTTTCTGAA GCCCCTCCCA GTTCTAGTTC         650

TATCTTTTTC CTGCATCCTG TCTGGAAGTT AGAAGGAAAC AGACCACAGA         700

CCTGGTCCCC AAAAGAAATG GAGGCAATAG GTTTTGAGGG GCATGGGGAC         750

GGGGTTCAGC CTCCAGGGTC CTACACACAA ATCAGTCAGT GGCCCAGAAG         800

ACCCCCCTCG GAATCGGAGC AGGGAGGATG GGGAGTGTGA GGGGTATCCT         850

TGATGCTTGT GTGTCCCCAA CTTTCCAAAT NCCCGCCCCC GCGATGGAGA         900

AGAAACCGAG ACAGAAGGTG CAGGGCCCAC TACCGCTTCC TCCAGATGAG         950

CTTATGGGTT TCTCCACCAA GGAAGTTTTC CGCTGGTTGA ATGATTCTTT        1000

CCCCGCCCTC CTCTCGCCCC AGGGACATAT AAAGGCAGTT GTTGGCACAC        1050

CCAGCCAGCA GACGCTCCCT CAGCAAGGAC AGCAGAGGAC CAGCTAAGAG        1100

GGAGAGAAGC AACTGCAGAC CCCCCCTGAA AACAACCCTC AGACGCCACA        1150

TCCCCTGACA AGCTGCCAGG CAGGTTCT                                1178
```

(2) INFORMATION FOR SEQ ID NO: 2:

(i) SEQUENCE CHARACTERISTICS:
        (A) LENGTH: 1096
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: human TNFa promoter gene (x) PUBLICATION INFORMATION:
        (A) AUTHORS: Takashiba, S., et al.
        (C) JOURNAL: Gene
        (D) VOLUME: 131
        (F) PAGES: 307-308

(xi) SEQUENCE DESCRIPTION: SEQ ID NO: 2:

```
GAGGCCGCCA GACTGCTGCA GGGGAAGCAA AGGAGAAGCT GAGAAGATGA          50

AGGAAAAGTC AGGGTCTGGA GGGGCGGGGG TCAGGGAGCT CCTGGGAGAT         100

ATGGCCACAT GTAGCGGCTC TGAGGAATGG GTTACAGGAG ACCTCTGGGG         150

AGATGTGACC ACAGCAATGG GTAGGAGAAT GTCCAGGGCT ATGGAAGTCG         200

AGTATGGGGA CCCCCCCTTA ACGAAGACAG GGCCATGTAG AGGGCCCCAG         250

GGAGTGAAAG AGCCTCCAGG ACCTCCAGGT ATGGAATACA GGGGACGTTT         300

AAGAAGATAT GGCCACACAC TGGGGCCCTG AGAAGTGAGA GCTTCATGAA         350
```

-continued

| | |
|---|---|
| AAAAATCAGG GACCCCAGAG TTCCTTGGAA GCCAAGACTG AAACCAGCAT | 400 |
| TATGAGTCTC CGGGTCAGAA TGAAAGAAGA AGGCCTGCCC CAGTGGGGTC | 450 |
| TGTGAATTCC CGGGGGTGAT TTCACTCCCC GGGGCTGTCC CAGGCTTGTC | 500 |
| CCTGCTACCC CCACCCAGCC TTTCCTGAGG CCTCAAGCCT GCCACCAAGC | 550 |
| CCCCAGCTCC TTCTCCCCGC AGGGACCCAA ACACAGGCCT CAGGACTCAA | 600 |
| CACAGCTTTT CCCTCCAACC CCGTTTTCTC TCCCTCAAGG ACTCAGCTTT | 650 |
| CTGAAGCCCC TCCCAGTTCT AGTTCTATCT TTTTCCTGCA TCCTGTCTGG | 700 |
| AAGTTAGAAG GAAACAGACC ACAGACCTGG TCCCCAAAAG AAATGGAGGC | 750 |
| AATAGGTTTT GAGGGGCATG GGGACGGGGT TCAGCCTCCA GGGTCCTACA | 800 |
| CACAAATCAG TCAGTGGCCC AGAAGACCCC CCTCGGAATC GGAGCAGGGA | 850 |
| GGATGGGGAG TGTGAGGGGT ATCCTTGATG CTTGTGTGTC CCCAACTTTC | 900 |
| CAAATCCCCG CCCCCGCGAT GGAGAAGAAA CCGAGACAGA AGGTGCAGGG | 950 |
| CCCACTACCG CTTCCTCCAG ATGAGCTCAT GGGTTTCTCC ACCAAGGAAG | 1000 |
| TTTTCCGCTG GTTGAATGAT TCTTTCCCCG CCCTCCTCTC GCCCCAGGGA | 1050 |
| CATATAAAGG CAGTTGTTGG CACACCCAGC CAGCAGACGC TCCCTC | 1096 |

(2) INFORMATION FOR SEQ ID NO: 3:

(i) SEQUENCE CHARACTERISTICS:
        (A) LENGTH: 139
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: native minimal TNFa promoter (xi) SEQUENCE DESCRIPTION: SEQ ID NO: 3:

| | |
|---|---|
| CCGCTTCCTC CAGATGAGCT CATGGGTTTC TCCACCAAGG AAGTTTTCCG | 50 |
| CTGGTTGAAT GATTCTTTCC CCGCCCTCCT CTCGCCCCAG GGACATATAA | 100 |
| AGGCAGTTGT ATGGCACACC CGCCAGCAGA CGCTCCCTC | 139 |

(2) INFORMATION FOR SEQ ID NO: 4:

(i) SEQUENCE CHARACTERISTICS:
        (A) LENGTH: 904
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp120 AIG.1
        (D) OTHER INFORMATION: residues 1 to 139 comprise the
            promoter sequence; residues 140 to 151, the linker
            sequence, and the remaining residues comprise the AIG.1
            sequence (xi) SEQUENCE DESCRIPTION: SEQ ID NO: 4:

| | |
|---|---|
| CCGCTTCCTC CAGATGAGCT CATGGGTTTC TCCACCAAGG AAGTTTTCCG | 50 |
| CTGGTTGAAT GATTCTTTCC CCGCCCTCCT CTCGCCCCAG GGACATATAA | 100 |
| AGGCAGTTGT TGGCACACCC AGCCAGCAGA CGCTCCCTCA GCAGATCCAC | 150 |

| | |
|---|---|
| CATGTCTGGA ATATCCCTGG ACAACAGTTA TAAAATGGAT TATCCTGAGA | 200 |
| TGGGTTTATG TATAATAATT AATAATAAGA ATTTTCATAA AAGCACTGGA | 250 |
| ATGACATCTC GGTCTGGTAC AGATGTCGAT GCAGCAAACC TCAGGGAAAC | 300 |
| ATTCAGAAAC TTGAAATATG AAGTCAGGAA TAAAAATGAT CTTACACGTG | 350 |
| AAGAAATTGT GGAATTGATG CGTGATGTTT CTAAAGAAGA TCACAGCAAA | 400 |
| AGGAGCAGTT TTGTTTGTGT GCTTCTGAGC CATGGTGAAG AAGGAATAAT | 450 |
| TTTTGGAACA AATGGACCTG TTGACCTGAA AAAAATAACA AACTTTTTCA | 500 |
| GAGGGGATCG TTGTAGAAGT CTAACTGGAA AACCCAAACT TTTCATTATT | 550 |
| CAGGCCTGCC GTGGTACAGA ACTGGACTGT GGCATTGAGA CAGACAGTGG | 600 |
| TGTTGATGAT GACATGGCGT GTCATAAAAT ACCAGTGGAG GCCGACTTCT | 650 |
| TGTATGCATA CTCCACAGCA CCTGGTTATT ATTCTTGGCG AAATTCAAAG | 700 |
| GATGGCTCCT GGTTCATCCA GTCGCTTTGT GCCATGCTGA AACAGTATGC | 750 |
| CGACAAGCTT GAATTTATGC ACATTCTTAC CCGGGCTAAC CGAAAGGTGG | 800 |
| CAACAGAATT TGAGTCCTTT TCCTTTGACG CTACTTTTCA TGCAAAGAAA | 850 |
| CAGATTCCAT GTATTGTTTC CATGCTCACA AAAGAACTCT ATTTTTATCA | 900 |
| CTAA | 904 |

(2) INFORMATION FOR SEQ ID NO: 5:

(i) SEQUENCE CHARACTERISTICS:
        (A) LENGTH: 1490
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp706 AIG.1
        (D) OTHER INFORMATION: residues 1 to 724 comprise the
            promoter sequence; residues 725 to 736, the linker
            sequence, and the remaining residues comprise the AIG.1
            sequence (xi) SEQUENCE DESCRIPTION: SEQ ID NO: 5:

| | |
|---|---|
| TCCTTGGAAG CCAAGACTGA AACCAGCATT ATGAGTCTCC GGGTCAGAAT | 50 |
| GAAAGAAGAA GGCCTGCCCC AGTGGGGTCT GTGAATTCCC GGGGGTGATT | 100 |
| TCACTCCCCG GGGCTGTCCC AGGCTTGTCC CTGCTACCCC CACCCAGCCT | 150 |
| TTCCTGAGGC TCAAGCCTGC CACCAAGCCC CCAGCTCCTT CTCCCCGCAG | 200 |
| GGACCCAAAC ACAGGCCTCA GGACTCAACA CAGCTTTTCC CTCCAACCCC | 250 |
| GTTTTCTCTC CCTCAAGGAC TCAGCTTTCT GAAGCCCCTC CCAGTTCTAG | 300 |
| TTCTATCTTT TTCCTGCATC CTGTCTGGAA GTTAGAAGGA AACAGACCAC | 350 |
| AGACCTGGTC CCCAAAAGAA ATGGAGGCAA TAGGTTTTGA GGGGCATGGG | 400 |
| GACGGGGTTC AGCCTCCAGG GTCCTACACA CAAATCAGTC AGTGGCCCAG | 450 |
| AAGACCCCCC TCGGAATCGG AGCAGGGAGG ATGGGGAGTG TGAGGGGTAT | 500 |
| CCTTGATGCT TGTGTGTCCC CAACTTTCCA AATCCCCGCC CCCGCGATGG | 550 |
| AGAAGAAACC GAGACAGAAG GTGCAGGGCC CACTACCGCT TCCTCCAGAT | 600 |
| GAGCTCATGG GTTTCTCCAC CAAGGAAGTT TTCCGCTGGT TGAATGATTC | 650 |

-continued

```
TTTCCCCGCC CTCCTCTCGC CCCAGGGACA TATAAAGGCA GTTGTTGGCA        700

CACCCAGCCA GCAGACGCTC CCTCAGCAGA TCCACCATGT CTGGAATATC        750

CCTGGACAAC AGTTATAAAA TGGATTATCC TGAGATGGGT TTATGTATAA        800

TAATTAATAA TAAGAATTTT CATAAAAGCA CTGGAATGAC ATCTCGGTCT        850

GGTACAGATG TCGATGCAGC AAACCTCAGG GAAACATTCA GAAACTTGAA        900

ATATGAAGTC AGGAATAAAA ATGATCTTAC ACGTGAAGAA ATTGTGGAAT        950

TGATGCGTGA TGTTTCTAAA GAAGATCACA GCAAAAGGAG CAGTTTTGTT        1000

TGTGTGCTTC TGAGCCATGG TGAAGAAGGA ATAATTTTTG GAACAAATGG        1050

ACCTGTTGAC CTGAAAAAAA TAACAAACTT TTTCAGAGGG GATCGTTGTA        1100

GAAGTCTAAC TGGAAAACCC AAACTTTTCA TTATTCAGGC CTGCCGTGGT        1150

ACAGAACTGG ACTGTGGCAT TGAGACAGAC AGTGGTGTTG ATGATGACAT        1200

GGCGTGTCAT AAAATACCAG TGGAGGCCGA CTTCTTGTAT GCATACTCCA        1250

CAGCACCTGG TTATTATTCT TGGCGAAATT CAAAGGATGC CTCCTGGTTC        1300

ATCCAGTCGC TTTGTGCCAT TGCTGAAACA GTATGCCGAC AAGCTTGAAT        1350

TTATGCACAT TCTTACCCGG GCTAACCGAA AGGTGGCAAC AGAATTTGAG        1400

TCCTTTTCCT TTGACGCTAC TTTTCATGCA AGAAACAGA TTCCATGTAT         1450

TGTTTCCATG CTCACAAAAG AACTCTATTT TTATCACTAA                   1490
```

(2) INFORMATION FOR SEQ ID NO: 6:

(i) SEQUENCE CHARACTERISTICS:
        (A) LENGTH: 1789
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp1005 AIG.1
        (D) OTHER INFORMATION: residues 1 to 1023 comprise the
            promoter sequence; residues 1024 to 1036, the linker
            sequence, and the remaining residues comprise the AIG.1
            sequence (xi) SEQUENCE DESCRIPTION: SEQ ID NO: 6:

```
GGCGGGGGTC AGGGAGCTCC TGGGAGATAT GGCCACATGT AGCGGCTCTG        50

AGGAATGGGT TACAGGAGAC CTCTGGGGAG ATGTGACCAC AGCAATGGGT        100

AGGAGAATGT CCAGGGCTAT GGAAGTCGAG TATGGGGACC CCCCCTTAAC        150

GAAGACAGGG CCATGTAGAG GGCCCCAGGG AGTGAAAGAG CCTCCAGGAC        200

CTCCAGGTAT GGAATACAGG GGACGTTTAA GAAGATATGG CCACACACTG        250

GGGCCCTGAG AAGTGAGAGC TTCATGAAAA AAATCAGGGA CCCCAGAGTT        300

CCTTGGAAGC CAAGACTGAA ACCAGCATTA TGAGTCTCCG GGTCAGAATG        350

AAAGAAGAAG GCCTGCCCCA GTGGGGTCTG TGAATTCCCG GGGGTGATTT        400

CACTCCCCGG GGCTGTCCCA GGCTTGTCCC TGCTACCCCC ACCCAGCCTT        450

TCCTGAGGCC TCAAGCCTGC CACCAAGCCC CCAGCTCCTT CTCCCCGCAG        500

GGACCCAAAC ACAGGCCTCA GGACTCAACA CAGCTTTTCC CTCCAACCCC        550

GTTTTCTCTC CCTCAAGGAC TCAGCTTTCT GAAGCCCCTC CCAGTTCTAG        600
```

```
TTCTATCTTT TTCCTGCATC CTGTCTGGAA GTTAGAAGGA AACAGACCAC           650

AGACCTGGTC CCCAAAAGAA ATGGAGGCAA TAGGTTTTGA GGGGCATGGG           700

GACGGGGTTC AGCCTCCAGG GTCCTACACA CAAATCAGTC AGTGGCCCAG           750

AAGACCCCCC TCGGAATCGG AGCAGGGAGG ATGGGGAGTG TGAGGGGTAT           800

CCTTGATGCT TGTGTGTCCC CAACTTTCCA AATCCCCGCC CCCGCGATGG           850

AGAAGAAACC GAGACAGAAG GTGCAGGGCC CACTACCGCT TCCTCCAGAT           900

GAGCTCATGG GTTTCTCCAC CAAGGAAGTT TTCCGCTGGT TGAATGATTC           950

TTTCCCCGCC CTCCTCTCGC CCCAGGGACA TATAAAGGCA GTTGTTGGCA          1000

CACCCAGCCA GCAGACGCTC CCTCAGCAGA TCCACCATGT CTGGAATATC          1050

CCTGGACAAC AGTTATAAAA TGGATTATCC TGAGATGGGT TTATGTATAA          1100

TAATTAATAA TAAGAATTTT CATAAAAGCA CTGGAATGAC ATCTCGGTCT          1150

GGTACAGATG TCGATGCAGC AAACCTCAGG GAAACATTCA GAAACTTGAA          1200

ATATGAAGTC AGGAATAAAA ATGATCTTAC ACGTGAAGAA ATTGTGGAAT          1250

TGATGCGTGA TGTTTCTAAA GAAGATCACA GCAAAAGGAG CAGTTTTGTT          1300

TGTGTGCTTC TGAGCCATGG TGAAGAAGGA ATAATTTTTG GAACAAATGG          1350

ACCTGTTGAC CTGAAAAAAA TAACAAACTT TTTCAGAGGG GATCGTTGTA          1400

GAAGTCTAAC TGGAAAACCC AAACTTTTCA TTATTCAGGC CTGCCGTGGT          1450

ACAGAACTGG ACTGTGGCAT TGAGACAGAC AGTGGTGTTG ATGATGACAT          1500

GGCGTGTCAT AAAATACCAG TGGAGGCCGA CTTCTTGTAT GCATACTCCA          1550

CAGCACCTGG TTATTATTCT TGGCGAAATT CAAAGGATGG CTCCTGGTTC          1600

ATCCAGTCGC TTTGTGCCAT GCTGAAACAG TATGCCGACA AGCTTGAATT          1650

TATGCACATT CTTACCCGGG CTAACCGAAA GGTGGCAACA GAATTTGAGT          1700

CCTTTTCCTT TGACGCTACT TTTCATGCAA AGAAACAGAT TCCATGTATT          1750

GTTTCCATGC TCACAAAAGA ACTCTATTTT TATCACTAA                      1789
```

(2) INFORMATION FOR SEQ ID NO: 7:

(i) SEQUENCE CHARACTERISTICS:
        (A) LENGTH: 1008
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp120 AIG.2
        (D) OTHER INFORMATION: residues 1 to 138 comprise the
            promoter sequence; residues 139 to 150, the linker
            sequence, and the remaining residues comprise the AIG.2
            sequence (xi) SEQUENCE DESCRIPTION: SEQ ID NO: 7:

```
CCGCTTCCTC CAGATGAGCT CATGGGTTTC TCCACCAAGG AAGTTTTCCG            50

CTGGTTGAAT GATTCTTTCC CCGCCCTCCT CTCGCCCCAG GGACATATAA           100

AGGCAGTTGT TGGCACACCC AGCCAGCAGA GCTCCCTCAG CAGATCCACC           150

ATGGCTGGAC CACCTGAGTC AGCAGAATCT ACAGATGCCC TCAAGCTTTG           200

TCCTCATGAA GAATTCCTGA GACTATGTAA AGAAAGAGCT GAAGAGATCT           250
```

```
ACCCAATAAA GGAGAGAAAC AACCGCACAC GCCTGGCTCT CATCATATGC           300

AATACAGAGT TTGACCATCT GCCTCCGAGG AATGGAGCTG ACTTTGACAT           350

CACAGGGATG AAGGAGCTAC TTGAGGGTCT GGACTATAGT GTAGATGTAG           400

AAGAGAATCT GACAGCCAGG GATATGGAGT CAGCGCTGAG GGCATTTGCT           450

ACCAGACCAG AGCACAAGTC CTCTGACAGC ACATTCTTGG TACTCATGTC           500

TCATGGCATC CTGGAGGGAA TCTGCGGAAC TGTGCATGAT GAGAAAAAAC           550

CAGATGTGCT GCTTTATGAC ACCATCTTCC AGATATTCAA CAACCGCAAC           600

TGCCTCAGTC TGAAGGACAA ACCCAAGGTC ATCATTGTCC AGGCCTGCAG           650

AGGTGCAAAC CGTGGGGAAC TGTGGGTCAG AGACTCTCCA GCATCCTTGG           700

AAGTGGCCTC TTCACAGTCA TCTGAGAACC TGGAGGAAGA TGCTGTTTAC           750

AAGACCCACG TGGAGAAGGA CTTCATTGCT TTCTGCTCTT CAACGCCACA           800

CAACGTGTCC TGGAGAGACA GCACAATGGG CTCTATCTTC ATCACACAAC           850

TCATCACATG CTTCCAGAAA TATTCTTGGT GCTGCCACCT AGAGGAAGTA           900

TTTCGGAAGG TACAGCAATC ATTTGAAACT CCAAGGGCCA AAGCTCAAAT           950

GCCCACCATA GAACGACTGT CCATGACAAG ATATTTCTAC CTCTTTCCTG          1000

GCAATTGA                                                        1008
```

(2) INFORMATION FOR SEQ ID NO: 8:

(i) SEQUENCE CHARACTERISTICS:
        (A) LENGTH: 1587
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp706 AIG.2
        (D) OTHER INFORMATION: residues 1 to 724 comprise the
            promoter sequence; residues 725 to 736, the linker
            sequence, and the remaining residues comprise the AIG.2
            sequence (xi) SEQUENCE DESCRIPTION: SEQ ID NO: 8:

```
TCCTTGGAAG CCAAGACTGA AACCAGCATT ATGAGTCTCC GGGTCAGAAT            50

GAAAGAAGAA GGCCTGCCCC AGTGGGGTCT GTGAATTCCC GGGGGTGATT           100

TCACTCCCCG GGGCTGTCCC AGGCTTGTCC CTGCTACCCC CACCCAGCCT           150

TTCCTGAGGC CTCAAGCCTG CCACCAAGCC CCCAGCTCCT TCTCCCCGCA           200

GGGACCCAAA CACAGGCCTC AGGACTCAAC ACAGCTTTTC CCTCCAACCC           250

CGTTTTCTCT CCCTCAAGGA CTCAGCTTTC TGAAGCCCCT CCCAGTTCTA           300

GTTCTATCTT TTTCCTGCAT CCTGTCTGGA AGTTAGAAGG AAACAGACCA           350

CAGACCTGGT CCCCAAAAGA AATGGAGGCA ATAGGTTTTG AGGGGCATGG           400

GGACGGGGTT CAGCCTCCAG GGTCCTACAC ACAAATCAGT CAGTGGCCCA           450

AAGACCCCCC TCGGAATCGG AGCAGGGAGG ATGGGGAGTG TGAGGGGTAT           500

CCTTGATGCT TGTGTGTCCC CAACTTTCCA AATCCCCGCC CCCGCGATGG           550

AGAAGAAACC GAGACAGAAG GTGCAGGGCC CACTACCGCT TCCTCCAGAT           600

GAGCTCATGG GTTTCTCCAC CAAGGAAGTT TTCCGCTGGT TGAATGATTC           650
```

```
TTTCCCCGCC CTCCTCTCGC CCCAGGGACA TATAAAGGCA GTTGTTGGCA          700

CACCCAGCCA GCAGACGCTC CCTCAGCAGA TCCACCATGG CTGGACCACC          750

TGAGTCAGCA GAATCTACAG ATGCCCTCAA GCTTTGTCCT CATGAAGAAT          800

TCCTGAGACT ATGTAAAGAA AGAGCTGAAG AGATCTACCC AATAAAGGAG          850

AGAAACAACC GCACACGCCT GGCTCTCATC ATATGCAATA CAGAGTTTGA          900

CCATCTGCCT CCGAGGAATG GAGCTGACTT GACATCACAG GATGAAGGAG          950

TACTTGAGGG TCTGGACTAT GTGTAGATGT GAAGAGAATC GACAGCCAGG         1000

ATATGGAGTC AGCGCTGAGG GCATTTGCTA CCAGACCAGA GCACAAGTCC         1050

TCTGACAGCA CATTCTTGGT ACTCATGTCT CATGGCATCC TGGAGGGAAT         1100

CTGCGGAACT GTGCATGATG AGAAAAAACC AGATGTGCTG CTTTATGACA         1150

CCATCTTCCA GATATTCAAC AACCGCAACT GCCTCAGTCT GAAGGACAAA         1200

CCCAAGGTCA TCATTGTCCA GGCCTGCAGA GGTGCAAACC GTGGGAACT          1250

GTGGGTCAGA GACTCTCCAG CATCCTTGGA AGTGGCCTCT TCACAGTCAT         1300

CTGAGAACCT GGAGGAAGAT GCTGTTTACA AGACCCACGT GGAGAAGGAC         1350

TTCATTGCTT TCTGCTCTTC AACGCCACAC AACGTGTCCT GGAGAGACAG         1400

CACAATGGGC TCTATCTTCA TCACACAACT CATCACATGC TTCCAGAAAT         1450

ATTCTTGGTG CTGCCACCTA GAGGAAGTAT TTCGGAAGGT ACAGCAATCA         1500

TTTGAAACTC CAAGGGCCAA AGCTCAAATG CCCACCATAG AACGACTGTC         1550

CATGACAAGA TATTTCTACC TCTTTCCTGG CAATTGA                       1587

(2) INFORMATION FOR SEQ ID NO: 9:

(i) SEQUENCE CHARACTERISTICS:
        (A) LENGTH: 1894
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: chimeric gene TNFp1005 AIG.2
        (D) OTHER INFORMATION: residues 1 to 1024 comprise the
            promoter sequence; residues 1025 to 1036, the linker
            sequence, and the remaining residues comprise the AIG.2
            sequence (xi) SEQUENCE DESCRIPTION: SEQ ID NO: 9:

GGCGGGGGTC AGGGAGCTCC TGGGAGATAT GGCCACATGT AGCGGCTCTG           50

AGGAATGGGT TACAGGAGAC CTCTGGGGAG ATGTGACCAC AGCAATGGGT          100

AGGAGAATGT CCAGGGCTAT GGAAGTCGAG TATGGGGACC CCCCCTTAAC          150

GAAGACAGGG CCATGTAGAG GGCCCCAGGG AGTGAAAGAG CCTCCAGGAC          200

CTCCAGGTAT GGAATACAGG GGACGTTTAA GAAGATATGG CCACACACTG          250

GGGCCCTGAG AAGTGAGAGC TTCATGAAAA AAATCAGGGA CCCCAGAGTT          300

CCTTGGAAGC CAAGACTGAA ACCAGCATTA TGAGTCTCCG GGTCAGAATG          350

AAAGAAGAAG GCCTGCCCCA GTGGGGTCTG TGAATTCCCG GGGGTGATTT          400

CACTCCCCGG GGCTGTCCCA GGCTTGTCCC TGCTACCCCC ACCCAGCCTT          450

TCCTGAGGCC TCAAGCCTGC CACCAAGCCC CCAGCTCCTT CTCCCCGCAG          500
```

```
GGACCCAAAC ACAGGCCTCA GGACTCAACA CAGCTTTTCC CTCCAACCCC         550

GTTTTCTCTC CCTCAAGGAC TCAGCTTTCT GAAGCCCCTC CCAGTTCTAG         600

TTCTATCTTT TTCCTGCATC CTGTCTGGAA GTTAGAAGGA AACAGACCAC         650

AGACCTGGTC CCCAAAAGAA ATGGAGGCAA TAGGTTTTGA GGGGCATGGG         700

GACGGGGTTC AGCCTCCAGG GTCCTACACA CAAATCAGTC AGTGGCCCAG         750

AAGACCCCCC TCGGAATCGG AGCAGGGAGG ATGGGGAGTG TGAGGGGTAT         800

CCTTGATGCT TGTGTGTCCC CAACTTTCCA AATCCCCGCC CCCGCGATGG         850

AGAAGAAACC GAGACAGAAG GTGCAGGGCC CACTACCGCT TCCTCCAGAT         900

GAGCTCATGG GTTTCTCCAC CAAGGAAGTT TTCCGCTGGT TGAATGATTC         950

TTTCCCCGCC CTCCTCTCGC CCCAGGGACA TATAAAGGCA GTTGTTGGCA        1000

CACCCAGCCA GCAGACGCTC CCTCAGCAGA TCCACCATGG CTGGACCACC        1050

TGAGTCAGCA GAATCTACAG ATGCCCTCAA GCTTTGTCCT CATGAAGAAT        1100

TCCTGAGACT ATGTAAAGAA AGAGCTGAAG AGATCTACCC AATAAAGGAG        1150

AGAAACAACC GCACACGCCT GGCTCTCATC ATATGCAATA CAGAGTTTGA        1200

CCATCTGCCT CCGAGGAATG GAGCTGACTT TGACATCACA GGGATGAAGG        1250

AGCTACTTGA GGGTCTGGAC TATAGTGTAG ATGTAGAAGA GAATCTGACA        1300

GCCAGGGATA TGGAGTCAGC GCTGAGGGCA TTTGCTACCA GACCAGAGCA        1350

CAAGTCCTCT GACAGCACAT TCTTGGTACT CATGTCTCAT GGCATCCTGG        1400

AGGGAATCTG CGGAACTGTG CATGATGAGA AAAAACCAGA TGTGCTGCTT        1450

TATGACACCA TCTTCCAGAT ATTCAACAAC CGCAACTGCC TCAGTCTGAA        1500

GGACAAACCC AAGGTCATCA TTGTCCAGGC CTGCAGAGGT GCAAACCGTG        1550

GGGAACTGTG GGTCAGAGAC TCTCCAGCAT CCTTGGAAGT GGCCTCTTCA        1600

CAGTCATCTG AGAACCTGGA GGAAGATGCT GTTTACAAGA CCCACGTGGA        1650

GAAGGACTTC ATTGCTTTCT GCTCTTCAAC GCCACACAAC GTGTCCTGGA        1700

GAGACAGCAC AATGGGCTCT ATCTTCATCA CACAACTCAT CACATGCTTC        1750

CAGAAATATT CTTGGTGCTG CCACCTAGAG GAAGTATTTC GGAAGGTACA        1800

GCAATCATTT GAAACTCCAA GGGCCAAAGC TCAAATGCCC ACCATAGAAC        1850

GACTGTCCAT GACAAGATAT TTCTACCTCT TTCCTGGCAA TTGA              1894
```

(2) INFORMATION FOR SEQ ID NO: 10:

(i) SEQUENCE CHARACTERISTICS:
        (A) LENGTH: 123
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: TNFa promoter enhancer region 1 (ER1)

(xi) SEQUENCE DESCRIPTION: SEQ ID NO: 10:

```
GGGGCGGGGG TCAGGGAGCT CCTGGGAGAT ATGGCCACAT GTAGCGGCTC          50

TGAGGAATGG GTTACAGGAG ACCTCTGGGG AGATGTGACC ACAGCAATGG         100

GTAGGAGAAT GTCCAGGGCT ATG                                      123
```

(2) INFORMATION FOR SEQ ID NO: 11:

(i) SEQUENCE CHARACTERISTICS:
        (A) LENGTH: 190
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: TNFa promoter enhancer region 2 (ER2)

(xi) SEQUENCE DESCRIPTION: SEQ ID NO: 11:

```
TCCTTGGAAG CCAAGACTGA AACCAGCATT ATGAGTCTCC GGGTCAGAAT          50

GAAAGAAGAA GGCCTGCCCC AGTGGGGTCT GTGAATTCCC GGGGGTGATT         100

TCACTCCCCG GGGCTGTCCC AGGCTTGTCC CTGCTACCCC CACCCAGCCT         150

TTCCTGAGGC CTCAAGCCTG CCACCAAGCC CCCAGCTCCT                    190
```

(2) INFORMATION FOR SEQ ID NO: 12:

(i) SEQUENCE CHARACTERISTICS:
        (A) LENGTH: 223
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: multiple cloning sites
        (D) OTHER INFORMATION: genetically engineered multiple
            cloning sites genetically engineered upstream of the
            minimal TNF promoter in the -120pGL3 construct (xi) SEQUENCE DESCRIPTION: SEQ ID NO: 12:

```
GGTACCGAGC TCTTACGCGT GCTAGCCGCG GATATCTTAA GACGTCCTAG          50

GACTAGTCAG CTGCTCGAGC CGCTTCCTCC AGATGAGCTC ATGGGTTTCT         100

CCACCAAGGA AGTTTTCCGC TGGTTGAATG ATTCTTTCCC CGCCCTCCTC         150

TCGCCCCAGG GACATATAAA GGCAGTTGTT GGCACACCCA GCCAGCAGAC         200

GCTCCCTCAG CAGATCTAAG CTT                                      223
```

(2) INFORMATION FOR SEQ ID NO: 13:

(i) SEQUENCE CHARACTERISTICS:
        (A) LENGTH: 787
        (B) TYPE: nucleic acid
        (C) STRANDEDNESS: single
        (D) TOPOLOGY: linear (ii) MOLECULE TYPE: <Unknown>
        (A) DESCRIPTION: DNA (ix) FEATURE:
        (A) NAME/KEY: TNFa 3' untranslated region (xi) SEQUENCE DESCRIPTION: SEQ ID NO: 13:

```
TCTAGAGGAG GACGAACATC CAACCTTCCC AAACGCCTCC CCTGCCCCAA          50

TCCCTTTATT ACCCCCTCCT TCAGACACCC TCAACCTCTT CTGGCTCAAA         100

AAGAGAATTG GGGGCTTAGG GTCGGAACCC AAGCTTAGAA CTTTAAGCAA         150
```

```
                                                        -continued

CAAGACCACC ACTTCGAAAC CTGGGATTCA GGAATGTGTG GCCTGCACAG          200

TGAAGTGCTG GCAACCACTA AGAATTCAAA CTGGGGCCTC CAGAACTCAC          250

TGGGGCCTAC AGCTTTGATC CCTGACATCT GGAATCTGGA GACCAGGGAG          300

CCTTTGGTTC TGGCCAGAAT GCTGCAGGAC TTGAGAAGAC CTCACCTAGA          350

AATTGACACA AGTGGACCTT AGGCCTTCCT CTCTCCAGAT GTTTCCAGAC          400

TTCCTTGAGA CACGGAGCCC AGCCCTCCCC ATGGAGCCAG CTCCCTCTAT          450

TTATGTTTGC ACTTGTGATT ATTTATTATT TATTTATTAT TTATTTATTT          500

ACAGATGAAT GTATTTATTT GGGAGACCGG GGTATCCTGG GGGACCCAAT          550

GTAGGAGCTG CCTTGGCTCA GACATGTTTT CCGTGAAAAC GGAGCTGAAC          600

AATAGGCTGT TCCCATGTAG CCCCCTGGCC TCTGTGCCTT CTTTTGATTA          650

TGTTTTTTAA AATATTTATC TGATTAAGTT GTCTAAACAA TGCTGATTTG          700

GTGACCAACT GTCACTCATT GCTGAGCCTC TGCTCCCCAG GGGAGTTGTG          750

TCTGTAATCG CCCTACTATT CAGTGGCGAG ATCTAGA                        787
```

SELF-REGULATED APOPTOSIS OF INFLAMMATORY CELLS

RELATED APPLICATION DATA

This application claims priority benefit of co-pending U.S. provisional Application serial No. 60/039,266, filed Feb. 28, 1997.

TECHNICAL FIELD OF THE INVENTION

This invention relates to the therapeutic induction of apoptosis in inflammatory cells by introducing into those cells a gene which induces apoptosis (programmed cell death or non-necrotic cell death) in these cells. The Apoptosis-Inducing Gene (which will sometimes be referred to herein as AIG) is driven by a TNFα promoter (TNFp) or other inducible gene activated in inflammation. In one embodiment, apoptosis is selectively induced in those cells capable of producing TNFα. The TNFp-AIG or other chimeric gene may be conveniently introduced in vivo using conventional gene therapy techniques. Advantageously, in the embodiment wherein the chimeric gene is TNFp-AIG, it is expressed in only those cells producing the inflammatory cytokine, TNFα. In addition, since the TNFp-AIG chimeric gene contains the TNFα promoter elements, it also sequesters inducible, TNFp-selective transcription factors. Such sequestration results in a reduction in endogenous production of TNFα. The present invention relates specifically to TNFp-AIG and similar gene constructs, cells containing chimeric genes, methods for induction of apoptosis in cells transfected with chimeric genes, pharmaceutical compositions containing chimeric genes, methods for in vitro selection of TNFα non-producer somatic cell variants within a TNFα producing cell population and the like, a method for identifying dominant negative/dominant suppressive genes responsible for inhibiting TNFα production and therapeutic methods using the chimeric gene.

BACKGROUND OF THE INVENTION

In many inflammatory conditions, cytokines such as IL-1, IL-10, GM-CSF and TNFα are excessively produced as a result of mass aggregation and accumulation of inflammatory cells (Brennan F. M. et al., British Medical Bulletin 1995, 51/2, 368–384). Upregulation and/or disregulation of cytokines in inflamed tissue may be directly or indirectly responsible for exacerbation of chronic inflammatory diseases. For example, the most marked pathology in rheumatoid arthritis (RA) is displayed at the local site of inflammation (i.e., the synovial joints). Therefore, it is likely that the cytokines produced in the synovial joints of RA patients play an important role in the disease process. Of those cytokines, IL-1 and TNFα are believed to be responsible for the devastating cartilage destruction and bone erosion which characterizes RA (Dayer J. M. et al., J. Exp. Med., 1985, 162, 1208–1215; Gowen M. et al., Nature, 1983, 306, 378–380). The presence of excessive amounts of IL-1 and TNFα in the synovial joints has been shown to accelerate development of collagen-induced arthritis in rodents (Brennan F. M., et al., Clin. Expt. Immunol., 1994, 97/1, 1–3). Excessive amounts of TNFα and IL-1 are produced in the synovial tissue by a variety of cell types at the cartilage-pannus junction, including cells of the macrophage lineage, macrophage-like synoviocytes, activated T-cells and possibly fibroblast-like synoviocytes (Chu C. Q. et al., Arthritis & Rheumatism, 1991, 34, 1125–1132; Deleuran B. W., et al., Arthritis & Rheumatism, 1992, 35, 1170–1178).

In addition to the above described inflammatory effects, TNFα plays a ubiquitous and key role in a variety of pro-inflammatory events, such as induction of IL-1 activity in monocytes. Indeed, anti-TNFα neutralizing antibodies have been shown to reduce overall IL-1 production (Portillo, et al., Immunol., 1989, 66, 170–175; Brennan F. M., et al., British Medical Bulletin 1995, 51/2, 368–384). Thus, an added benefit to blocking the effect of the inflammatory cytokine TNFα is the reduction in production of the equally destructive pro-inflammatory mediator, IL-1. Furthermore, it is well known that TNFα is a transcriptional activator of other inflammation-related genes. For example, the presence of TNFα stimulates production of other cytokines (such as GM-CSF) and cell surface receptors, including HLA class II antigens and adhesion molecules (Alvaro-Garcia J. M., et al., J. Exp. Med., 1989, 146, 865–875), which, results in continuous recruitment of activated T cells and neutrophils resulting in synovial inflammation and hyperplasia and ultimately, in augmented destruction of cartilage and bone (Allen J. B., J. Exp. Med., 1990, 171, 231).

Conventional therapy against inflammatory disorders is typically directed against symptomatic inflammation. Such therapies provide only temporary relief without significantly delaying disease progression. In contrast, therapies targeting TNFα and other factors induced in the inflammatory process are likely to be more promising. For example, in collagen-induced arthritis animal models, an anti-TNFα antibody and soluble TNFα receptor-IgG chimera effectively reduced paw swelling, joint involvement and cartilage and bone destruction (Williams R. O. et al., Proc. Natl. Acad. Sci., 1992, 89, 9784–9788). Human trials using both humanized anti-TNFα antibodies and TNFα receptor-IgG chimeric molecules produced dramatic results (Elliott M. J., et al., Arthritis and Rheumatism, 1993, 36, 1681–1690; Elliott M. J., et al., Lancet, 343, 1105–1110). Although treatment with these TNFα antagonists appears to be well tolerated, it also results in production of antibodies against the recombinant proteins. Thus, these therapies may not be suitable for long term treatment and do not achieve true disease abatement. In order to actually modify progression of the disease, TNFα must be continuously targeted using TNFα-specific therapies. Such a therapeutic protocol is impractical with these biologic agents and would be difficult to administer in the long term.

In an alternate therapeutic option, inflamed synovium may be removed using surgical (Herold N. and Schroder H. A., Acta Orthop. Scand., 1995, 66, 252–254; Ogilvie-Harris D. J. and Weisleder L., Arthroscopy, 1995, 11, 91–95), chemical (Cruz-Esteban C. and Wilke W. S., Bailliere's Clinical Rheumatol., 1995, 9, 787–801) or radiation-induced synovectomy (Cruz-Esteban C. and Wilke W. S., Bailliere's Clinical Rheumatol., 1995, 9, 787–801). The results following arthroscopic surgical synovectomy are good, showing improvement from the preoperative condition to the postoperative condition. Non-surgical synovectomy is performed using various chemical agents such as osmic acid, alkylating agents such as nitrogen mustard and thiotepa, methotrexate. Unfortunately, non-surgical synovectomies (including chemical and radiation-induced) are procedurally complicated, provide only short term relief and show only patchy reduction of the synovial hyperplasia. Furthermore, most of the non-surgical alternatives are potential teratogens. In addition, the chemical damage to afflicted tissue in non-surgical synovectomy, as well as surgically-induced tissue damage, often cause an inflammatory response themselves. Finally, it should be noted that these approaches suffer from the risks and side-effects commonly associated with conventional pharmaceutical therapy and invasive surgical procedures, including the expense and inconvenience of hospitalization and rehabilitation.

Accordingly, a need still exists for an effective therapeutic approach to treating inflammatory disorders in general and RA in particular.

SUMMARY OF THE INVENTION

This invention overcomes the drawbacks associated with previous therapies for treating inflammatory disorders by providing a novel therapeutic approach. According to one embodiment of this invention, apoptosis is selectively induced in TNFα-producing inflammatory cells, causing destruction of these cells without an associated inflammatory reaction.

One objective of this invention is to provide a therapeutic method comprising the step of introducing into the inflammatory cells of a mammal, or cells at a site of inflammation, a chimeric gene containing a self-regulating apoptosis-inducing gene (AIG). The AIG is driven by a promoter such as a TNFα promoter (TNFp; see FIGS. 1 and 2), and, preferably, a promoter enhancer. Therefore, it is expressed in all and only those cells capable of producing TNFα.

Another objective of this invention is to provide TNFp-AIG and the like chimeric gene constructs, processes for making them, methods of using them, and preparations containing them.

Yet a further objective of this invention is to provide a method for the induction of apoptosis in cells transfected with the TNFp-AIG chimeric gene, a method for the in vitro selection of TNFα non-producer somatic cell variants in a population, a method for identifying dominant/negative genes responsible for the genesis of a TNFα non-producing population and a method for identifying products responsible for regulation of TNFα production (FIG. 10).

These and other objectives will be readily appreciated by those of ordinary skill in the art based upon the following detailed disclosure of the invention.

DETAILED DESCRIPTION OF THE INVENTION

Figure 1:
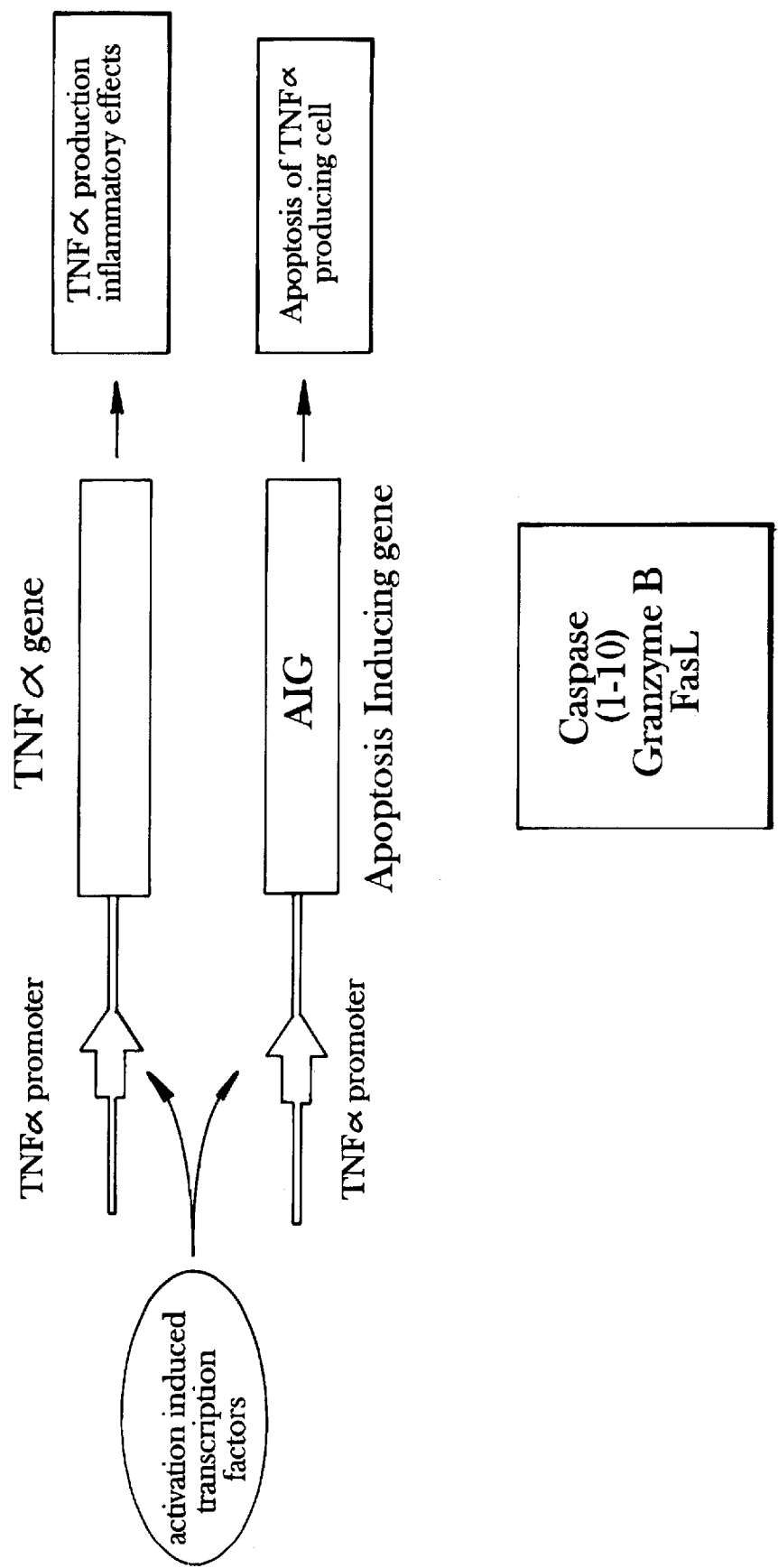
FIG. 1 is a schematic representation of TNFp-AIG chimeric genes of this invention. Apoptosis Inducing Gene (AIG) could be any, but not limited to, the genes listed, viz., Caspases 1 to 10, Granzyme B, FasLigand, etc.
Figure 2:
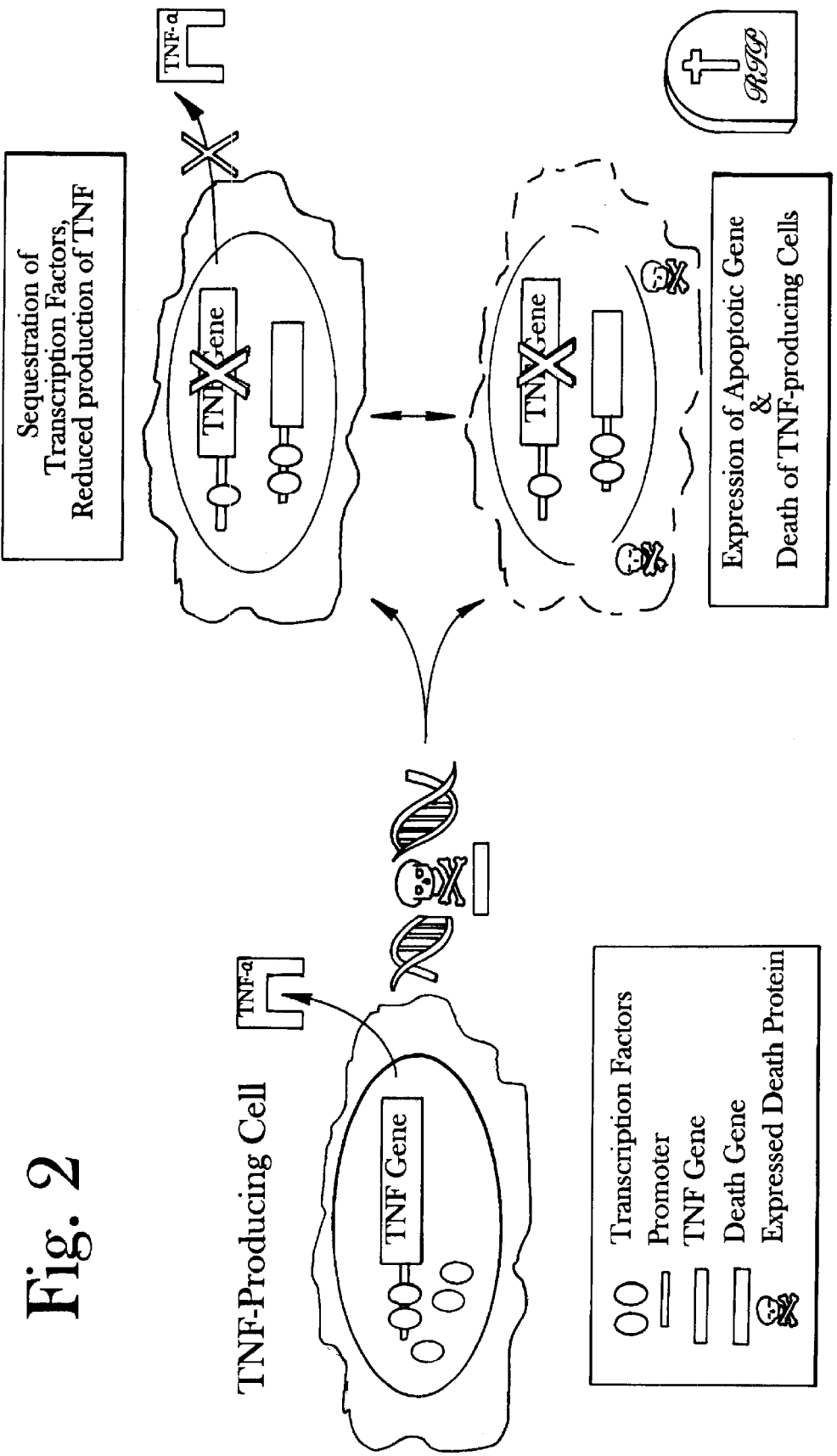
FIG. 2 is a schematic drawing depicting the results of gene therapy using a TNFp-AIG chimeric genes of this invention.

This invention is based upon evidence that apotosis of inflammatory cells in certain inflammatory diseases is therapeutically beneficial. The invention specifically relates to self-regulated apoptosis by gene therapy. Broadly speaking, in the practice of the invention, a chimeric gene comprising at least one promoter enhancer attached to at least one functional copy of a minimal promoter, the promoter being a gene or combination of genes activated in inflammatory cells or in cells at a site of inflammation, is attached to at least one copy of an apoptosis-inducing gene (AIG), such that the expression of the apoptosis-inducing gene is driven by the promoter, thus targeting the inflammatory cells. Example promoters of inducible genes activated in inflammation include, but are not limited to, cytokines, interleukins and their receptors, cell adhesion molecules and their ligands, chemokines and their receptors, pro-inflammatory enzymes, and the like. Chimeric genes according to the invention comprise enhancer, promoter, and AIG elements in direct, distal, or proximal attachment, and combinations thereof. As mentioned above and will be discussed in more detail below, in some embodiments, multiple copies of the enhancer, promoter, and/or AIG are employed for maximal efficacy.

In order that the invention herein described may be more fully understood, the following detailed description is set forth, with emphasis on chimeric genes comprising at least one TNFα promoter enhancer attached to at least one functional copy of a minimal TNFα promoter and further attached to at least one copy of an AIG for illustrative purposes only. Though the examples that follow also employ these types of constructions, it will be appreciated by skilled workers that the basic constructs described herein may be altered to provide other embodiments that utilize products, processes, methods, and compositions of the invention with other promoters comprising inducible genes activated in inflammation such as the types listed above that exhibit similar functions that can be used to target cells at the site of infection.

For example, cytokines and interleukins useful as promoters in the construction of chimeric genes of the invention include, but are not limited to, TNF-α, TNFβ, IL-1α, IL-1β, IL-2, IL-6, IL-9, GM-CSF, interferonγ, and the like, and functional fragments and mixtures thereof. Cell adhesion molecules and their ligands include, but are not limited to, selecting, integrins, and members of the immunoglobulin superfamily such as ICAM-1, V-CAM, and the like, and functional fragments and variants and mixtures thereof. Chemokines and their receptors include, but are not limited to, the C-X-C and C-C family members such as MIP-1α, MIP-1β, MCP1-4, RANTES, Mig, NAP2, IP10, Gro α-γ and the like, and functional fragments and variants and mixtures thereof. Pro-inflammatory enzymes include, but are not limited to COX-2, iNOS, phospholipases, proteases (including matrix metalloproteases), and the like and functional fragments and mixtures thereof.

To clarify the discussion below of exemplary TNFp-AIG chimeric genes of this invention, the following sequences are illustrated:

SEQ ID NO: 1 is the nucleotide sequence corresponding to the full-length, reference human TNFα promoter sequence, as published in (Takashiba S., et al., *Gene*, 1993, 131, 307–308). Nucleotide numbers used herein refer to the numbering of this sequence.

SEQ ID NO: 2 is the native TNFα promoter sequence of the gene that was used in this invention (–1077 nucleotides from the transcription start site, TSS). There are a few differences in the sequence of the TNFp in SEQ ID NO: 1 and SEQ ID NO: 2. Such differences in the nucleotide sequences of the TNFα promoter have been reported (Takashiba S., et al., *Gene*, 1993, 131, 307–308).

SEQ ID NO: 3 is the native minimal TNFα promoter sequence (nucleotide –120 through –TSS, which includes at least one enhancer element (k1 site; see Pauli, U., *Crit. Rev. in Eucaryotic Gene Expression*, 1994, 4, 323–344; Rhoades K. L., et al., *J. Biol. Chem.*, 1992, 267, 22102–22107; and Takashiba S., et al., *Gene*, 131, 307–108).

SEQ ID NO: 4 is the chimeric gene TNFp120 AIG.1 (containing –120 TNFp driving the expression of the prodomain-deleted variant of CPP32 gene (Caspase 3, published Tewari M. et al., *Cell*, 1995, 81(5), 801–809, with the variation being V239A).

SEQ ID NO: 5 is the chimeric gene TNFp706 AIG.1 (containing –706TNFp driving expression of the prodomain-deleted CPP 32 gene.

SEQ ID NO: 6 is the TNFp1005 AIG.1 (containing –1005 TNFp driving expression of the prodomain-deleted CPP 32 gene).

SEQ ID NO: 7 is the chimeric gene TNFp120AIG.2 (containing –120 TNFp driving expression of the prodomain-deleted Ty/x gene. (Sequences of Ty (Caspase 5) and Tx (Caspase 4) genes are published in the ref. Faucheu, C., et. al., *Eur. J Biochem.*, 236, 207–213, 1996; Faucheu, C., et. al. *EMBO J.*, 14, 1914–1922,1995).

SEQ ID NO: 8 is the chimeric gene TNFp706 AIG.2 (containing –706TNFp driving expression of the prodomain-deleted Ty/x gene.

SEQ ID NO: 9 is the TNFp1005 AIG.1 (containing –1005 TNFp driving expression of the prodomain-deleted Ty/x gene).

SEQ ID NO: 10 is the enhancer region 1 (ER1) of the TNFα promoter encompassing nucleotides –1005 to –905.

SEQ ID NO: 11 is the enhancer region 2 (ER2) of the TNFα promoter encompassing nucleotides –706 to –517.

SEQ ID NO: 12 is additional multiple cloning sites (MCS) genetically engineered upstream of the –120 minimal TNFα promoter in the –120pGL3 construct.

SEQ ID NO: 13 is the 3' untranslated region (3'UTR) of the TNFα gene (Nedwin, G. E., et al., *Nucleic Acid Research*, 1985, 13, 6361–6373).

The elements of the TNFα promoter for preparation of chimeric gene constructs according to this invention are selected from elements which are capable of inducing expression of a therapeutic gene driven by the TNFα promoter. These promoter elements will be referred to herein as "inducible cis elements", "cis-inducible elements" or "enhancer elements" of the TNFα promoter.

The enhancer elements may be physically linked to the minimal promoter sequence, or separated from the minimal promoter by a linker sequence which may or may not have unique restriction sites. Thus, as summarized above, enhancer elements may be attached directly, distally, proximally, or any combination thereof, to chimeric genes of the invention. These are typically constructed upstream of the promoter. Example TNFα enhancer elements are set out in SEQ ID NO: 10 and SEQ ID NO: 11; functional fragments or variants and combinations thereof may be employed. Some preferred gene constructs according to this invention include those that have multiple copies of the enhancer elements, i.e., 2 or more copies. Some embodiments have about 2 to 25, more narrowly 2 to 10, and even more narrowly, 2 to 5 copies.

The terms "TNF promoter", "TNFα promoter" and "TNFp" are used interchangeably herein. Unless noted to the contrary, these terms refer to the entire nucleotide sequence corresponding to a native TNFα minimal promoter sequence attached to one or more upstream enhancer elements (either present naturally i.e. native, or genetically engineered in the laboratory). Examples include, but are not limited to, SEQ ID NO: 1, SEQ ID NO: 2, and SEQ ID NO: 3, and functional fragments, variants, and mixtures of any of these. Many functional fragments and variants of these TNFα sequences and others described herein share a sequence homology of at least about 80%, and in some cases over 90%, to their native and genetically engineered counterparts, but these are known to skilled workers and defined in the references cited herein.

Any apoptosis-inducing gene may be used in the chimeric genes and methods described herein. The apoptosis inducing gene used for the chimeric therapeutic genes of this invention can be the same or different from the type of apoptosis inducing gene present in the native sequence of the TNF-α-producing inflammatory cells (if those cells naturally contain an apoptotic gene). Preferred AIGs include, but are not limited to, members of the ICE/CED3 family of apoptosis inducing proteases (such as Caspase-1 (ICE), hICE, ICE-LAP45, Mch2α), Caspase-2 (ICH1), Caspase-3

(CPP32, Yama, Apopain), Caspase-4 (TX, ICH2, ICE rel II), Caspase-5 (ICE rel III, TY), Caspase-6 (Mch-2), Caspase-7 (Mch-3, ICE-LAP3, CMH-1), Caspase-8 (MACH, FLICE, Mch-5), Caspase-9 (ICE-LAP6, Mch6) and Caspase-10 (Mch4)), members of the granzyme family (such as Granzyme A and Granzyme B), Fas ligand (FasL), and functional fragments, variants, and mixtures of any of these. Some embodiments employ Caspase 3, Caspase 4, Caspase 5, Granzyme B, and functional fragments, variants, and mixtures thereof. With the exception of FasL, these genes, when overexpressed following transfection, induce apoptosis in the transfected cells (Miura M., et al., *Cell,* 1993, 75, 653–660; Chinnayan A. M., et al., *Cell,* 1995, 81, 505–512; Los, et al., *Nature,* 1995, 375, 81; Muzio, et al., *Cell,* 1996, 85, 817–827).

In the case of FasL, apoptosis is induced (either in an autocrine or a paracrine fashion) in only those cells that express Fas. Therefore, the TNFp-FasL chimeric gene construct offers a second level of selectivity. Another advantage of the TNFp-FasL chimeric gene is the selective targeting of those disease-producing cells in the synovium that do not express TNFα (thereby failing to drive expression of the apoptosis inducing gene), but do express Fas on the surface. In this case, FasL will be expressed by the cells that are capable of producing TNFα such as activated macrophages and T cells. These cells will then induce apoptosis in Fas-expressing cells such as hazardous activated T cells and Fas-expressing synoviocytes.

This invention provides a novel therapeutic method comprising the step of introducing into the cells of a mammal a chimeric gene comprising an apoptosis-inducing gene (AIG) driven by the TNFα promoter (TNFp). Example chimeric genes of the invention are set out in SEQ ID NOs 4, 5, 6, 7, 8, and 9; functional fragments or variants of these may also be employed. Without wishing to be bound by theory, as a result of being controlled by the TNFp, AIG is expressed in only those cells producing the inflammatory cytokine, TNFα. Therefore, any cells expressing TNFα will be self-destructive, while cells that do not express TNF-α will be unaffected. Advantageously, this methodology can target any TNFα-producing cells (such as activated macrophages, activated T-cells and macrophage-like and possibly fibroblast-like synoviocytes) without regard to cell type. Indeed, the targeted TNFα-producing cell can be one which normally does or normally does not carry or expresses an apoptosis gene in its native, unaltered form. Therefore, using the chimeric genes and methods of this invention, the cellular sources of TNFα can be destroyed in a highly selective manner.

Another advantage of using the TNFp-AIG chimeric gene of this invention is that TNFp sequesters transcription factors needed by endogenous TNFp, thereby leading to a reduction in endogenous TNFα production. In one preferred embodiment, TNFp is present in the therapeutically targeted cell in vast excess. This may be accomplished by introducing multiple copies of the transfected gene into the cell. Alternatively, the TNFp-AIG chimeric gene according to this invention can contain multiple copies of the inducible cis elements of the TNFα promoter. As mentioned above, multiple copies of the "inducible enhancer elements" of TNFp are present in some embodiments of the TNFp-AIG chimeric genes of this invention. By including multiple copies of the inducible cis elements of the TNFp construct, the transcriptional factors needed by the transfected cell to produce TNFα are sequestered by the exogenously introduced sequence. This preferred chimeric TNFp-AIG construct is characterized by an increased effectiveness in competing for the TNFp-specific transcription factors as compared to chimeric genes of this invention containing only a single enhancer element linked to TNFp. The "inducible super promoter" constructed in this way is capable of (1) more effectively competing for TNFα specific inducible transcription factors and (2) driving expression of the apoptosis inducing gene in an augmented fashion by virtue of multiple enhancing elements.

For example, in rheumatoid arthritis patients, synovectomy, i.e., removal of synovial tissue, has been shown to be clinically beneficial. Unlike conventional and surgical synovectomy procedures, the cell-targeted therapeutic method described herein targets only cells producing TNFα. Thus, advantageously, the introduction and expression of the TNFp-AIG chimeric gene, and subsequent induction of apoptosis do not induce an inflammatory response. Accordingly, methods of this invention are comparatively selective and result in minimal tissue damage and a reduction in inflammation.

The products and methods described herein are useful for the treatment of other inflammatory disorders as well. Such inflammatory disorders include, but are not limited to, multiple sclerosis, Guillain-Barre syndrome, Crohn's disease, ulcerative colitis, psoriasis, graft versus host disease, lupus erythematosus, insulin-dependent diabetes mellitus, psoriatic arthritis, sarcoidosis, hypersensivity pneumonitis, ankylosing spondylitis and related spoldyloarthropathies, Reiter's syndrome and systemic sclerosis. Thus, this invention encompasses methods for treating an inflammatory disorder in a patient by inducing apoptosis in inflammatory cells or cells at a site of inflammation of the patient by introducing into the cells at least one chimeric gene of the invention. This is typically accomplished by preparing a pharmaceutical composition containing at least one chimeric gene of the invention and typically a pharmaceutically acceptal carrier, and administering the composition to a patient using standard means. In some embodiments, the pharmaceutical composition is delivered directly to the site of inflammation using local topical, intravenous, intraperitoneal, and similar methods. Further methodology is discussed below.

In addition to the therapeutic indications, the genes and cells according to this invention can be used in a variety of useful screening and selection methods. In one such method, TNFα non-producer somatic cell variants within a TNFα producing cell population can be selected in vitro by introducing a TNFp-AIG chimeric gene into the TNFα producing cell population. Cells producing TNFα will undergo apoptosis. Cells that do not produce TNFα will survive. Selection of those cell variants possessing the survival phenotype is an easy way to identify TNF-α non-producer cells. Such a selection process may be used to determine expression of genes that act in-trans to regulate activity of the TNF-α promoter, thereby reducing TNF-α production. Such genes are characterized as dominant negative (DN)/dominant suppressive genes in other systems (Behrends S., et al., *J. Biol. Chem.* 1995, 270, 21109–21113; Zhang S., et al., *J. Biol. Chem.,* 1995, 270, 23934–23936; Watowich S. S., et al., *Mol. Cell Biol.,* 1994, 14/6, 3535–3549).

In a further in vitro method, a TNFp-AIG chimeric gene according to this invention can be used to identify dominant negative genes responsible for the genesis of a TNFα non-producing cell population. According to this method, a TNFp-AIG chimeric gene according to this invention is introduced into cells that produce TNFα. Barring the presence of a dominant negative gene, those cells should undergo apoptosis upon activation. Therefore, it can be deduced that surviving variants possess a dominant negative gene capable of down-regulating TNFα production. The dominant negative gene can be readily identified by producing a cDNA library and transfecting cell lines (e.g., Jurkat and THP-1). These cells are either stable transfectants of an inducible TNFp-AIG chimeric gene or TNFp-luciferase gene TNFp-AIG transfected cells will be selected for the survival phenotype following in vitro activation; survival phenotype is indicative of the effect of the DN genes. In the cells transfected with TNFp-luciferase gene, reduction in the luciferase activity will be indicative of the DN gene effect. Dominant negative genes identified using this protocol can be used as the future therapeutic agents themselves. Such genes will be the candidates for gene therapy in order to reduce TNFα production.

The methods utilized for gene transfer are grouped into two broad categories:

1. Direct approach: In situ transduction of the therapeutic gene into target cells such as synoviocytes using a suitable vector as a carrier for the therapeutic gene. The vector containing therapeutic gene is injected directly into the affected area (e.g., an arthritic joint).
2. Indirect approach: Ex-vivo transfection of the therapeutic gene into target cells such as synoviocytes. In this approach, the synovium is removed from joints, synoviocytes are isolated and cultured in vitro. In vitro cultured cells are transfected with the therapeutic gene, and genetically modified synoviocytes are transplanted back into the synovium.

For in vivo transfer, several vectors have been evaluated for their efficacy in gene delivery (Nita, et al., *Arthritis & Rheumatism*, 1996, 39/5, 820–828). Among the vectors used for gene therapy, the vectors derived from retroviruses are by far the best developed. They are able to insert genetic material in the host genome and produce stable transfectants. These vectors, however are unable to infect non-dividing cells and, since they are inserted in the host genome, the possibility of insertional mutagenesis cannot be ruled out. In comparison, the vectors derived from adenoviruses infect dividing as well as non-dividing cells and deliver DNA episomally. The disadvantage of adenovirus based vectors is that these vectors continue to produce viral proteins in infected cells making them potentially antigenic. A third type of viral based vectors is derived from Herpes simplex viruses (HSV), which are also capable of infecting dividing as well as non dividing cells.

Among the non-viral vector systems, cationic liposomes and naked plasmid DNA have been evaluated. Liposomes are at the most advanced stage of development, although certain types of cells such as muscle and skin take up, retain and express naked plasmid DNA.

Particle-mediated gene-delivery system is also possible (Rakhmilevich, et al., *PNAS*, 1996, 93, 6291) and is a promising approach.

The following "in vivo" gene delivery protocols can be used to deliver the chimeric genes of this invention:

(1) Nita et al., *Arthritis and Rheumatism*, 1996, 39, 820–823
  In vivo experiment in rabbits: Each vector is injected intra-articularly into 1 knee joint. For viral vectors, between $10^8$ and $10^9$ particles suspended in 0.5 ml balance salt solution are injected per knee.
  Liposome-DNA complexes (200 nmoles of DC-Chol complexed with 20 µg of DNA/ml) in 1 ml balance salt solution are injected per knee.

(2) *Methods in Molecular Medicine: Gene Therapy Protocols*, Paul Robbins, ed., 1997, Barr et al., pages 205–212

Adenovirus-based vector delivery to hepatocytes: Rat hepatocytes $1 \times 10^{11}$ PFU in 100 g animal.
  In dogs (12–17 kg), portal vein is perfused with about $1.5 \times 10^{11}$ PFU/kg gives 1 adenovirus genome copy per diploid copy of host DNA
  In rabbits (2–4kg), $1.5 \times 10^{13}$ virus particles (about $1.5 \times 10^{11}$ PFU) gives 100% hepatocyte transduction; $4 \times 10^{12}$ virus particles give 50–75% transduction.

Yang N-S, et al., 281–296
  Gold particle-mediated gene delivery: Transfection of mammalian skin tissue-0.1, 0.5, 1.0 and 2.5 µg of DNA/mg particle gives linear relationship with transgene expression levels.

Nabel, et al., 297–305
  Liposome-mediated gene delivery in humans:
    Protocol 1: 15 nmol DC-Chol/Dope liposomes combined with 1 µg DNA in 0.7 ml. 0.2 ml of the above mixture is injected into the patient's melanoma nodule. For catheter delivery, 0.6 ml of the solution is delivered into the artery.
    Protocol 2: 15 nmol DMRIE/Dope liposomes combined with 5 µg DNA in 1.0 ml.
  For direct intra-tumor injections, DNA concentrations range from 3 µg complexed with 4.5 nM DMRIE/Dope to 300 µg complexed with 450 nM DMRIE/Dope.

(3) Roessler, et al. 369–374
  Gene transfer to synovium:
    A range of doses, $10^9$–$10^{12}$ adenovirus particles containing therapeutic gene/joint are used. However, the optimal dose for any particular experimental series needs to be determined empirically, and is dependent on both the properties of the recombinant adenoviral genomic backbone being used as well as the transgene being expressed.

For the indirect approach, a variety of methods are well established, including utilization of cationic lipid or cationic polymer-based transfection and electroporation.

Any of the above-referenced techniques can be altered to suit the particular needs of those of ordinary skill in the art. Such modifications are well within the level of skill possessed by ordinary practitioners and do not require undue experimentation. These obvious variations are within the scope of this invention.

EXAMPLES

In order that this invention be more fully understood, the following examples are set forth. These examples are for the purpose of illustrating some preferred embodiments of this invention, and are not to be construed as limiting the scope of this invention in any way.

Example 1

Production of TNFp-AIG Constructs

In order to construct chimeric AIG driven by the enhancer cis elements of the TNF promoter, either in a single or multiple copies of the same region or various regions, identification of the regions of interest responsible for optimal inducible expression of the reporter gene is performed.

Figure 3:
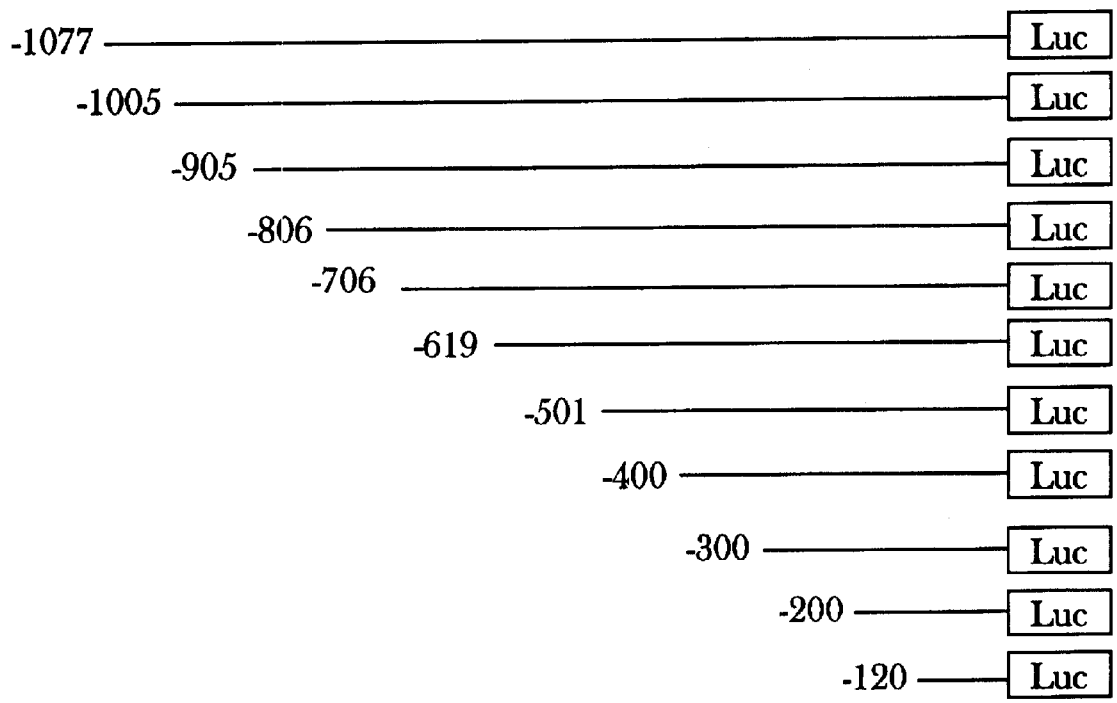
FIG. 3 is a summary of deletion constructs used for identification of the inducible cis elements of the TNFα promoter using luciferase gene (Luc) expression as the reporter system.
Figure 4A:
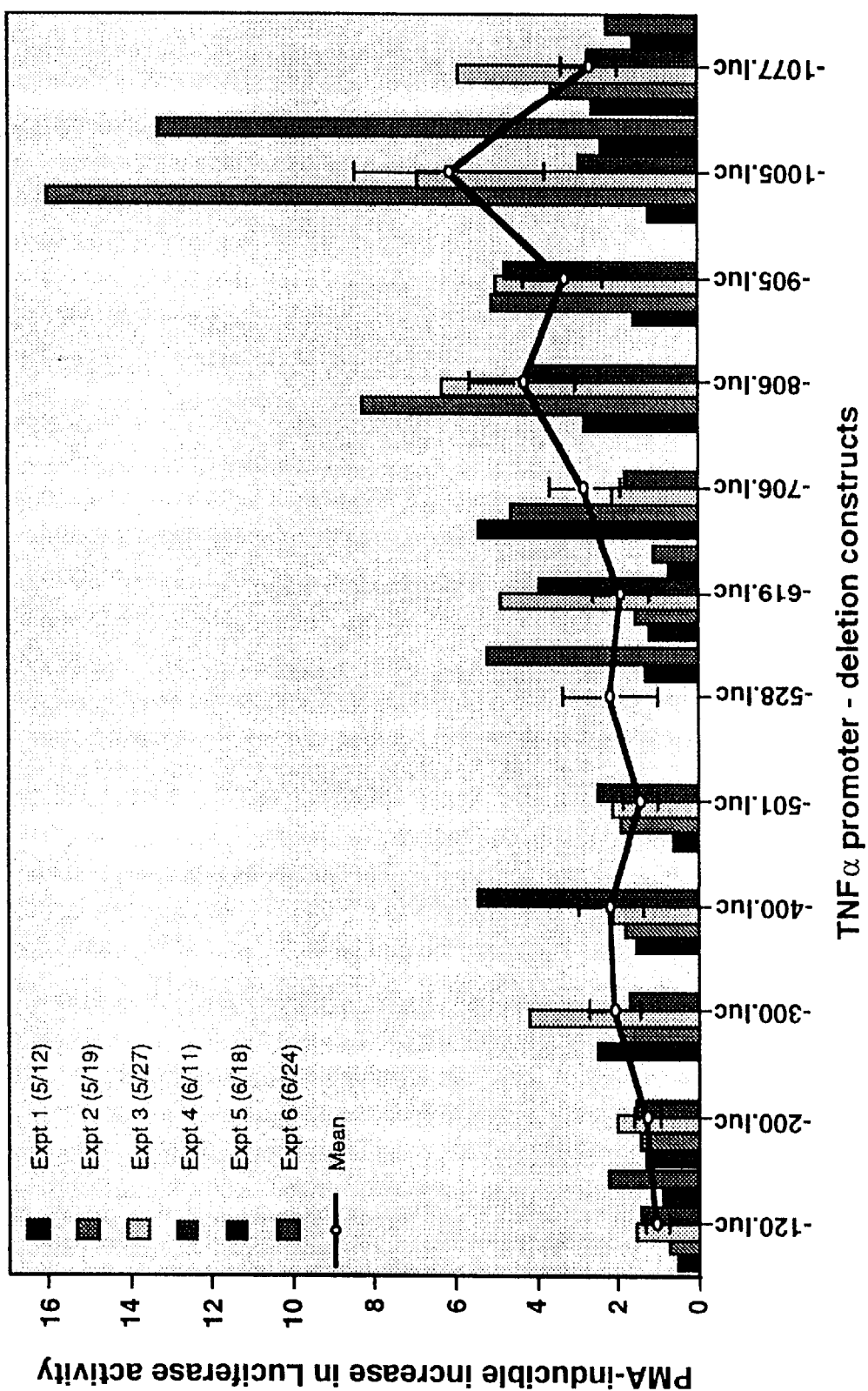
FIGS. 4(a and b) provide a summary of results obtained using the constructs described in FIG. 3. Transient expression of the constructs was assessed in two different TNFα-producing cell lines, viz., Jurkat (FIG. 4a) and THP-1 (FIG. 4b). Histograms in each figure show stimulation index as a measure of inducibility by activating agents such as PMA (FIG. 4a) or LPS (FIG. 4b) for individual experiments. The line superimposed in each figure indicates the mean inducibility averaged from 4 to 6 experiments.

Selection of the TNF-α promoter elements for constructing a chimeric gene. The regions of the TNF-α promoter are amplified by polymerase chain reaction (PCR) using primers encompassing various deletion constructs of the TNFα promoter (FIG. 3). The regions identified by other investigators in various other cellular systems are used as reference (Rhoades, et al., *J. Biol. Chem.*, 1992, 267, 22102–22107;

Leitman, et al., *Mol. Cell Biol.,* 1992, 12, 1352–1356; Pauli U., *Crit. Reviews Eukaryotic Gene Expression,* 1994, 4, 323–344). The PCR-amplified genes are then cloned upstream of a reporter gene, such as luciferase, in a commercially available promoterless vector. These constructs are tested for their constitutive and inducible expression in various cell lines such as Jurkat (T lymphoblastoid), U973 (myelomonocytic), THP-1 (monocytic), fibroblasts and in vitro cultured human synoviocytes. Identification of the regions responsible for inducible expression of the reporter gene is primarily based on the results obtained using two TNFα-producing cell lines, viz Jurkat (following stimulation with PMA) and THP-1 (following stimulation with LPS) (FIGS. 4a and b). These cells are transiently transfected by using well established methods and commercially available reagents, e.g., DEAE dextran and Superfect. The cis-elements of the TNFα promoter that are responsible for inducible expression of the reporter gene are then used for constructing TNFp-AIG chimeric genes.

Construction of TNFp-AIG chimeric genes. Of the apoptosis inducing genes described herein, the following genes are preferred:
i) cysteine protease—CPP32 (also known as Yama, apopain or Caspase 3) and
ii) Cysteine protease—Tx/Ty (Caspase 4/Caspase 5)

The AIGs are used as "prodomain-deleted" truncations in order to potentially augment autocatalysis of Caspases. This is essential for conversion of inactive Caspase to active form.

Prodomain-deleted CPP32 is amplified using primers corresponding to codons 29–36 and 271–278 (278 is a stop codon). The truncated form of CPP32 is referred to as "αCPP32" or "AIG.1" herein.

For PCR amplification for prodomain-deleted Ty, primers corresponding to the sequences in the Ty gene are synthesized. All Caspases discovered so far have homology to the other members of the Caspase family. The 3' primer corresponding to the codons 359–365 (codon 365 is a stop codon ) shares 100% sequence homology to the codons 372–378 (codon 378 is a stop codon) in the Tx gene. However, the 5' primer corresponding to codons 81–87 in the Ty gene does not share 100% homology with the corresponding region in the Tx gene (Tx codons 94–100). Residue 87 (Alanine) in the Ty gene differs from residue 100 (Glycine) in the Tx gene. The PCR amplified product generated from cDNA prepared from activated human peripheral blood lymphocytes possesses the sequence of Tx, due to apparent abundance of Tx transcripts. Therefore, the truncated form of the AIG generated using synthetics oligonucleotide primers corresponding to the sequences in Ty, indeed matches sequences in Tx, albeit flanked by Ty sequences of the primers. The Ty sequences of the primers used also match with the sequence of Tx, except for one codon. Thus the gene used in this invention matches truncated Tx gene with residue G100 toA change. This gene is referred to as "ΔTy/x" or "AIG.2" herein.

Figure 5:
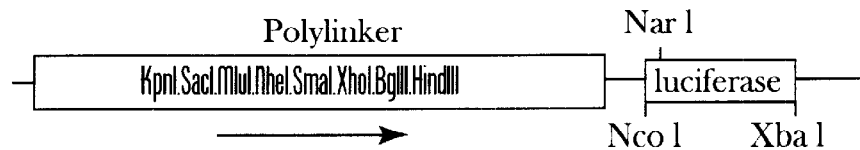
FIG. 5 is a flow chart for preparation of the TNFpAIG using selected native elements of the TNFα promoter and prodomain-deleted AIGs (AIGs used are Caspase and Caspase 4/5).
Figure 5:
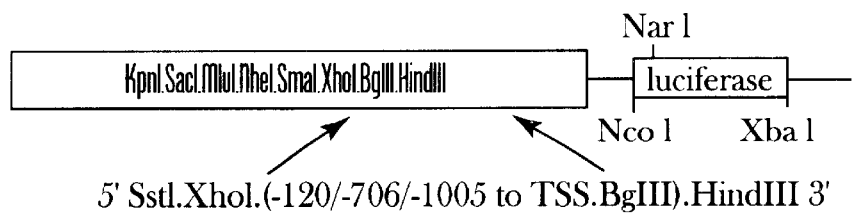
Figure 5:
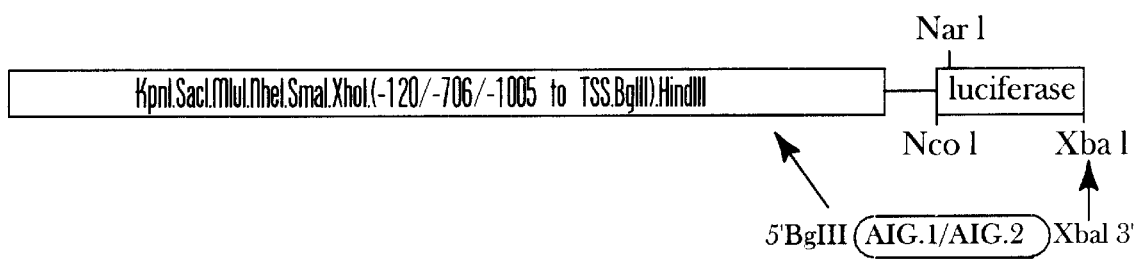
Figure 6A:
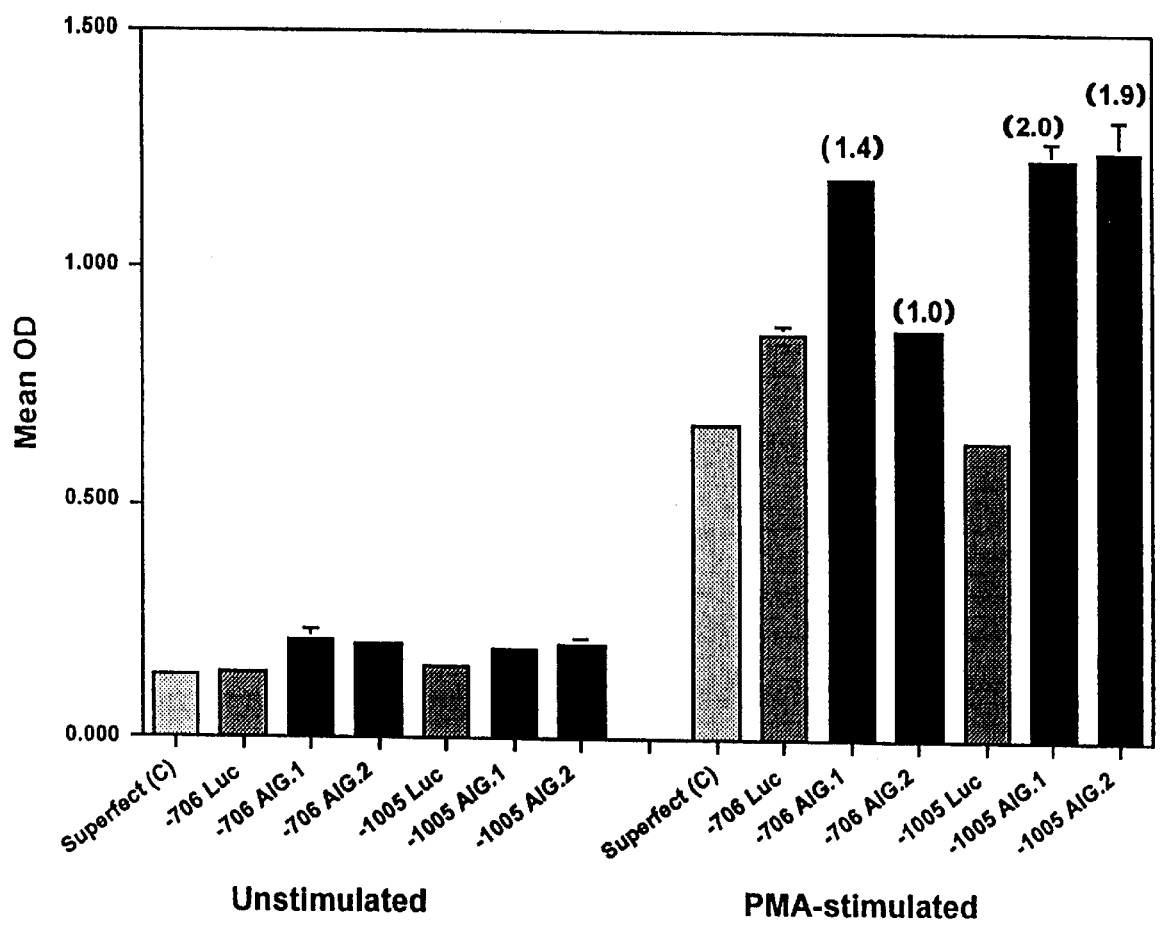
FIGS. 6(a, b, and c) provide a summary of results from representative experiments performed to see expression of the chimeric TNFpAIGs. Apoptosis in transiently-transfected Jurkat cells (FIGS. 6a and 6b) and THP-1 (FIG. 6c) cells was assessed using Cell Death Elisa (CDE assay). In all three figures, histograms with sparse dots represent transfection control, where cells were treated with the transfecting agent in the absence of DNA. Histograms with dense dots represent the TNFp elements driving expression of the luciferase gene and solid histograms represent the same TNFp elements driving expression of either AIG.1 or AIG.2. The number in parenthesis above the solid histograms represent enrichment factor (ratio of apoptosis induced by TNFpAIG to the TNFpLuc control vector).
Figure 6B:
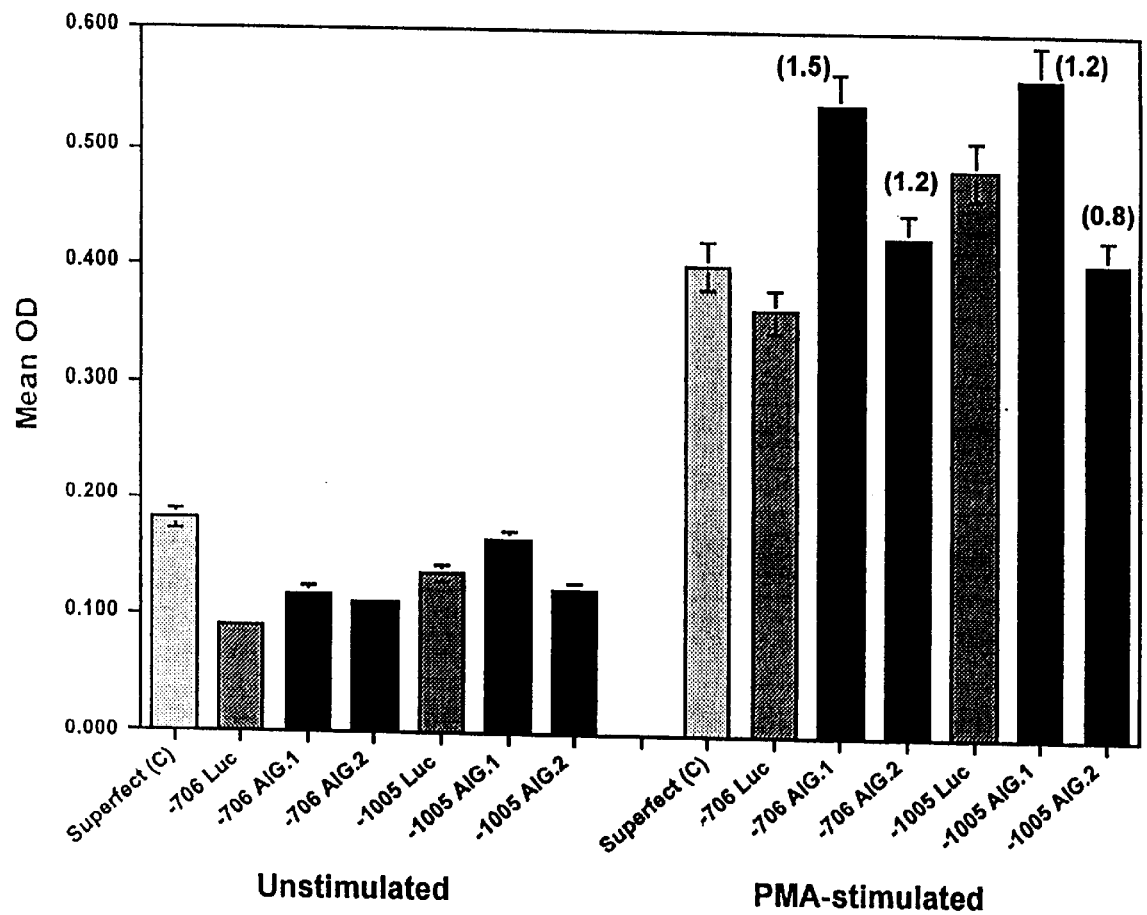
Figure 6C:
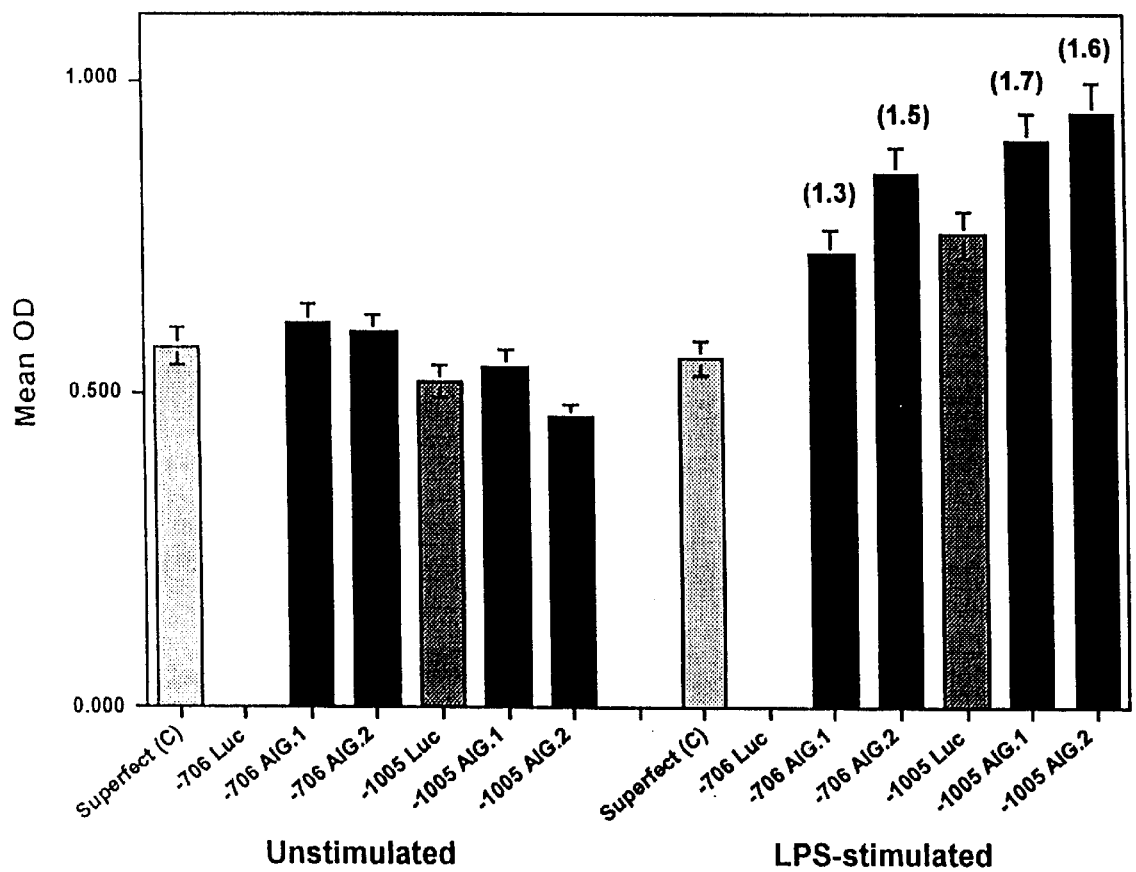

AIG.1 and AIG.2 are inserted downstream of the TNFα promoter by replacing the luciferase reporter gene in deletion constructs (−120, −706 and −1005) of the TNFα promoter (FIG. 5). These constructs are tested for the induction of apoptosis following stimulation of transiently-infected Jurkat and THP-1 cells (FIGS. 6a, b, and c).

Figure 4B:
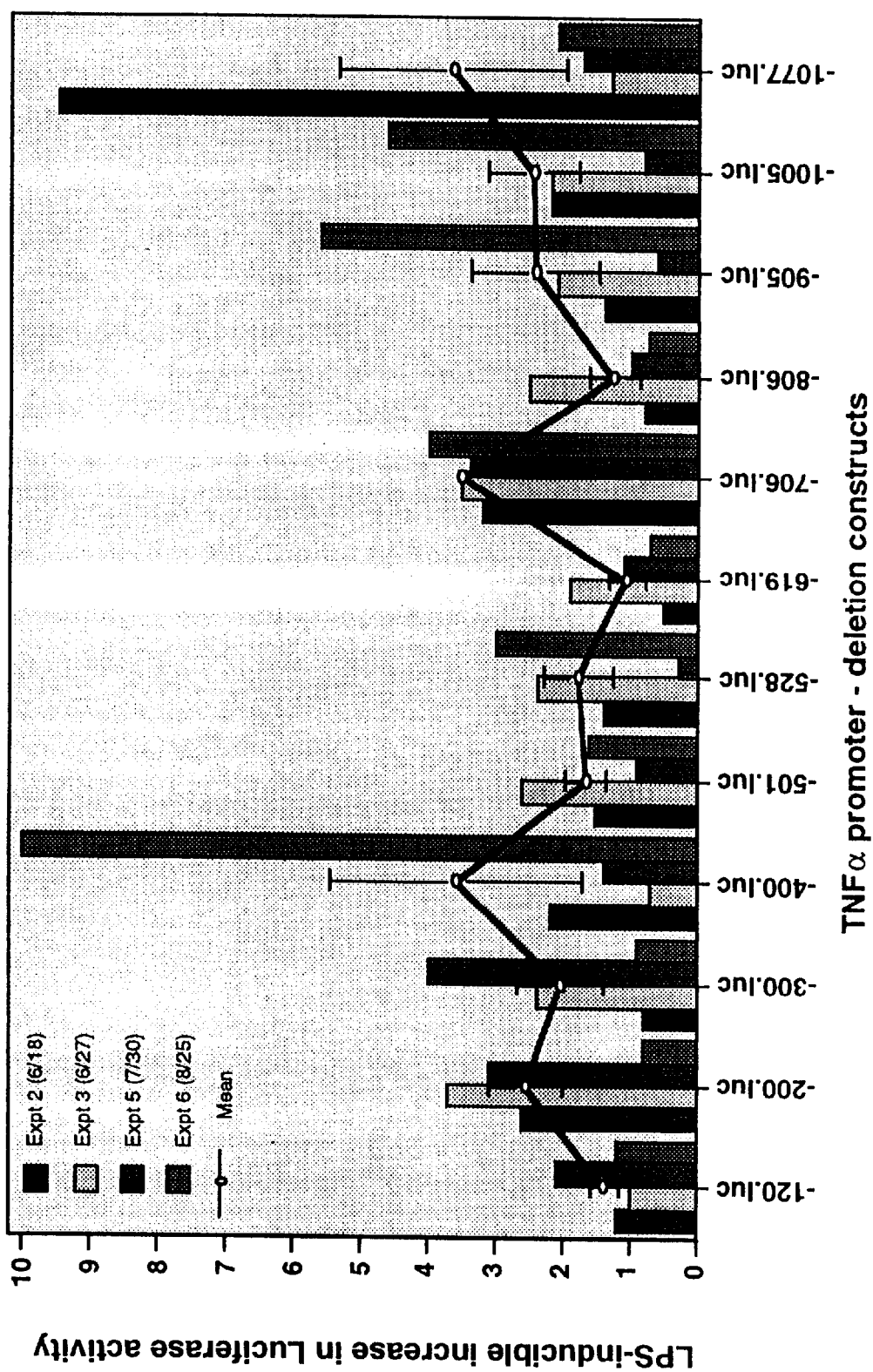
Figure 7:
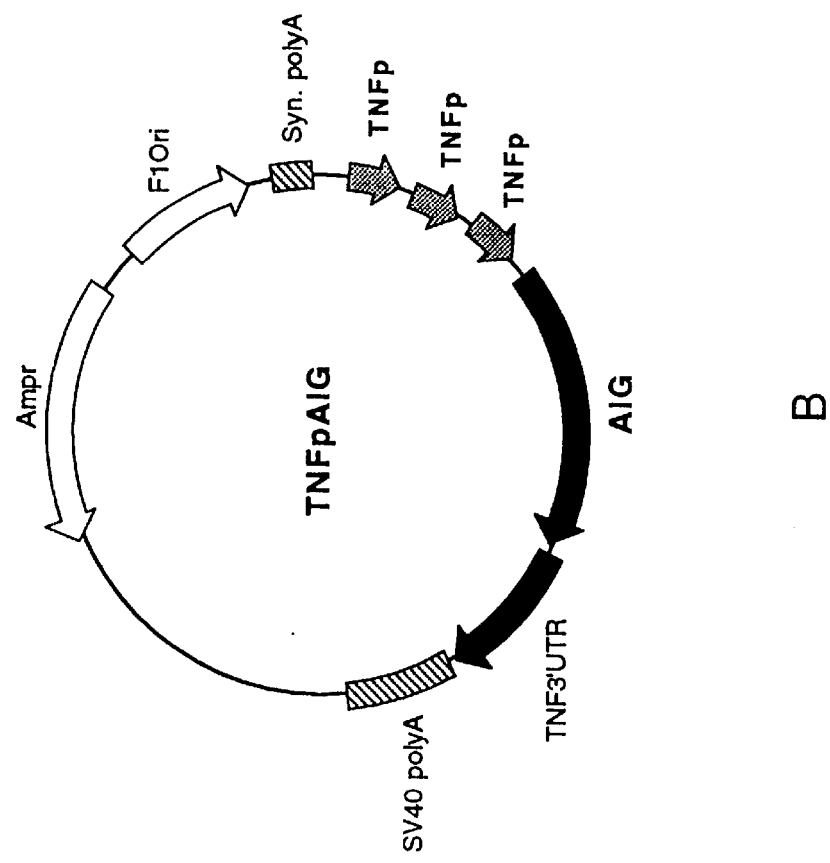
FIGS. 7(a and b) is a diagrammatic representation of a TNFp-AIG chimeric gene of this invention, comprising multiple copies of the inducible cis elements of the TNFα promoter which, in turn, drive expression of the AIG (FIG. 7a). A diagrammatic representation of a TNFpAIG chimeric gene, comprising multiple copies of the inducible cis elements of the TNFα promoter, driving expression of the AIG, downstream of which are 3' untranslated region of the TNFα gene (TNF3'UTR) (FIG. 7b). 3'UTR of the TNFα gene is implicated in the regulation of the inducible expression of TNFα (Han, J., et al., *J. Immunology,* 1991, 146, 1843–1843, Crawford, E. K., et al., *J. Biol. Chem.,* 1997, 272, 21120–21137, and FIG. 9).
Figure 7:
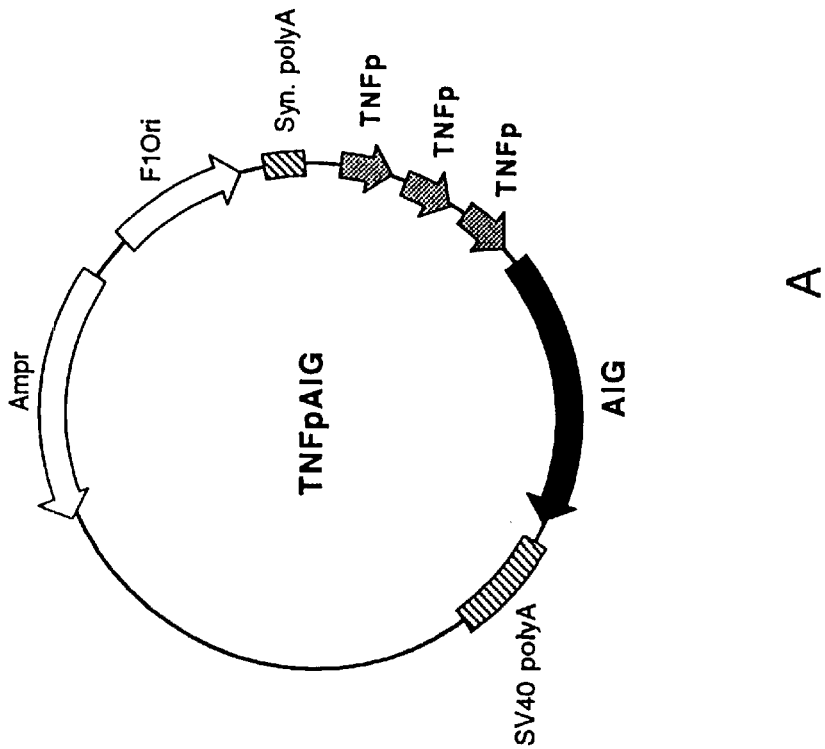

Constuction of TNFα superpromoter-AIG chimeric genes. Two broad preferred regions, viz., ER1(−1005 to −905) (SEQ. ID 10) and ER2(−706 to −517) (SEQ ID NO: 11) of the TNFα promoter, containing elements responsible for inducible expression of the reporter gene described above (FIGS. 4a and 4b) are PCR amplified and are ligated upstream of the minimal native promoter (−120 through TSS, SEQ ID NO: 3), either as a single copy or multiple copies. Two more regions (−234 to −120) and (−234 to −65) of the TNFα promoter is also identified as a potential enhancer region 3 (ER3) and enhancer region 4 (ER4), respectively, which can be employed in the chimeric constructs using the strategies described below. The super promoter contains multiple (2–10) cassettes of the above mentioned regions containing inducible promoter elements (FIG. 7). This is achieved by PCR amplifying the regions of interest using primers synthesized with restriction sites inserted at the 5' end of each of the primers. These unique restriction sites flank the amplified gene product of interest. Preferably, PCR amplified AIG is cloned downstream of the TNF-(super promoter, replacing the luciferase reporter gene in the original construct as described (FIG. 5) for the native TNFα promoter.

Figure 8A:
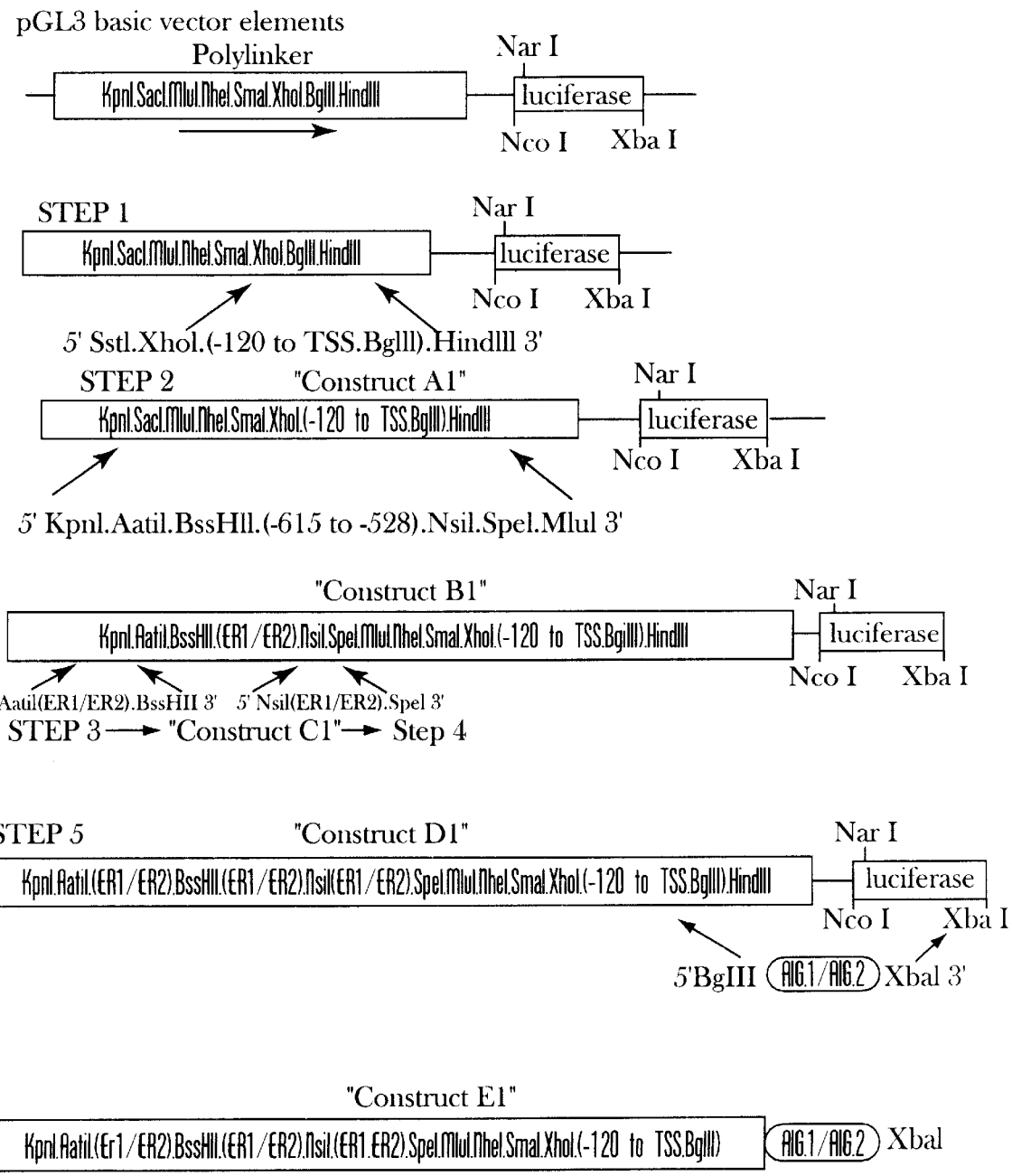
FIGS. 8(a and b) are flow charts of schemes for preparing TNFα superpromoter-AIG chimeric constructs.
Figure 8B:
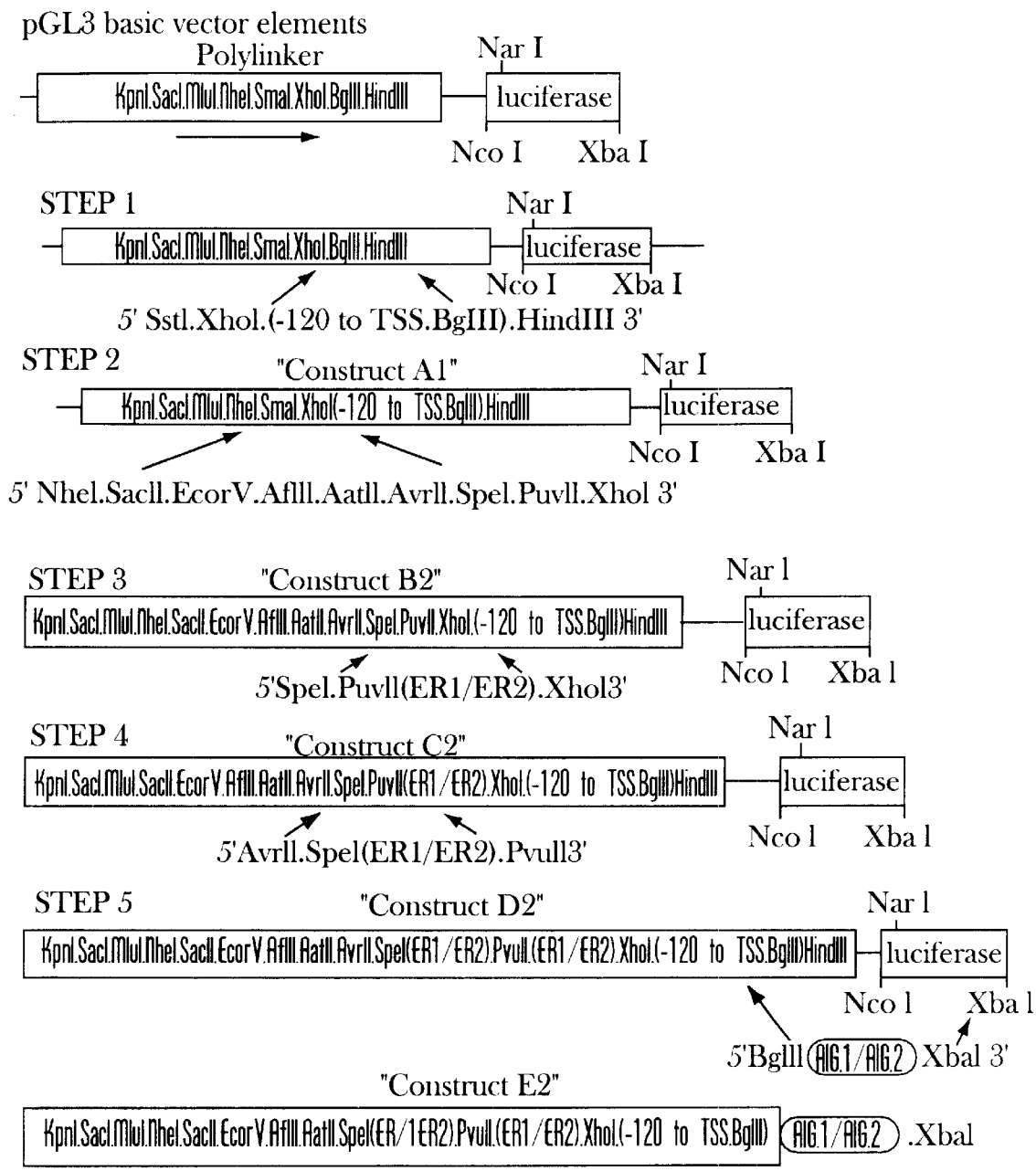

The schemes for construction of a TNFα superpromoter and the linker sequences representing unique restriction sites (these restriction sites are absent in the selected elements of the TNF-α promoter and the AIG in question) for efficient directional insertion is outlined below and depicted in FIG. 8:

Scheme 1
STEP 1: Insertion of the TNF-α minimal promoter (−120 to TSS) into the pGL3 basic (promoterless) luciferase vector (Promega):

The elements of pGL3 basic vectors that are used for construction of the chimeric gene TNFp-AIG are shown below.
_KpnI.SacI.MluI.NheI.SmaI.XhoI.BglII.HindIII. [luciferase].XbaI_

The minimal promoter is PCR amplified using primers containing XhoI and BglII.HindIII sites, so that XhoI is at the 5'end and BglII.HindIII sites are at the 3' end of the amplified product. This fragment is inserted into the polylinker of the pGL3 basic vector using these same restriction sites. This construct is referred to as "Construct A1" and is as follows:
_KpnI.SacI.MluI.NheISmaIXhoI.(−120 to TSSBglII) .HindIII.[luciferase].XbaI_

STEP 2: The enhancer fragment (ER1 or ER2) is PCR amplified using the primer containing several restriction sites. The resulting fragment will have restriction sites KpnI.AatII.BssHII at the 5' end and NsiI.SpeI.MluI at the 3'end as follows: 5' KpnI.AatII.BssHII.(ER1 or ER2) .NsiI.SpeI.MluI 3". The fragment is inserted into the "Construct A1" generated in STEP 1 using KpnI and MluI restriction sites. This construct is referred to as "Construct B1" and is as follows:
_KpnI.AatII.BssHII.(ER1 or ER2). NsiI.SpeI.MluI.NheI.SmaI.XhoI(−120 to TSS BglII) .HindIII. [luciferase].XbaI_

STEP 3: The TNFα enhancer fragment (ER1 or ER2)) is amplified using the primers containing restriction sites AatII and BssHII to generate the PCR product as follows:
5' AatII.(ER1 or ER2).BssHII 3'. This fragment is cloned into the "Construct B1" using these same restriction sites. This construct is referred to as "Construct C1" and is as follows:
_KpnI.AatII.(ER1 or ER2).BssHII.(ER1 or ER2) .NsiI.SpeI.MluI.NheI SmaI.XhoI(−120 to TSS BglII) .HindIII.[luciferase].XbaI_

STEP 4: The TNFα enhancer fragment (ER1 or ER2) is amplified using the primers containing restriction sites NsiI and SpeI to generate the PCR product as follows:

5' NsiI.(ER1 or ER2).SpeI 3'. This fragment will be cloned into the "Construct C1" using these same restriction sites. This construct is referred to as "Construct D1" and is as follows:

_KpnI.AatII.(ER1 or ER2).BssHIII.(ER1 or ER2).NsiI. (ER1 or ER2).SpeI.MluI.NheI SmaI.XhoI(−120 to TSSBglII).HindIII.[luciferase].XbaI STEP 5: AIG.1 or AIG.2 (preferred but not limited to AIG.1 and AIG.2; any AIG from the list can be used) coding regions are PCR-amplified using the primers containing BglII and XbaI restriction sites generating the fragment as follows: 5' BglII.(AIG.1 or AIG.2).XbaI 3". This fragment is inserted into the "Construct D1" using these same restriction sites. The resulting construct is referred to as "Construct E1" and is as follows:

_KpnI.AatII.(ER1 or ER2).BssHIII.(ER1 or ER2).NsiI. (ER1 or ER2).SpeI.MluI.NheI.SmaI.XhoI(−120 to TSS.BglII)[AIG.1 or AIG.2].XbaI_

Alternatively scheme 2 is followed:

Scheme 2

STEP 1: Same as in scheme I giving rise to "Construct A1", which is as follows:

KpnI.SacI.MluI,NheI.SmaI.XhoI.(−120 to TSS BglII) .HindIII.[luciferase].XbaI

STEP 2: Insertion of additional MCS.

Two complementary oligonucleotides (5' phosphorylated) providing

_NheI.SacII.EcorV.AflII.AatII.AvrII.SpeI.PvuII.XhoI_ are synthesized using commercial sources. These oligonucleotides are annealed and then cloned into NheI and XhoI sites of the "Construct A1". The resulting construct referred to as "Construct B2" and it is as follows:

_KpnI.SacI.MluI.NheI.SacII.EcorV.AflII.AatII.AvrII.SpeI.-PvuII.XhoI.(−120 to TSS BglII).HindIII.[luciferase] .XbaI_

STEP 3: The TNF-α enhancer fragment (ER1 or ER2) is amplified using the primers containing restriction sites SpeI.PvuII at the 5' end, and XhoI at the 3' end to generate the PCR product as follows: 5' SpeI.PvuII.(ER1 or ER2). XhoI 3'. This fragment is cloned into the "Construct B2" using SpeI and XhoI restriction sites. This construct is referred to as "Construct C2" and is as follows:

_KpnI.SacI.MluI.NheI. SacII.EcorV.AflII.AatII.AvrII.SpeI.PvuII.(ER1 or ER2) XhoI.(−120 to TSS BglII).HindIII.[luciferase].XbaI_

STEP 4: The TNFα enhancer fragment (ER1 or ER2) is amplified using the primers containing restriction sites AvrII. SpeI at the 5' end, and and PvuII at the 3' end to generate the PCR product as follows: 5' AvrII.SpeI.(ER1 or ER2).PvuII 3'. This fragment is cloned into the "Construct C2" using AvrII and PvuII restriction sites. This construct is referred to as "Construct D2" and is as follows:

_KpnI.SacI.MluI.NheI. SacII.EcorV.AflII.AatII.AvrII.SpeI. (ER1 or ER2) PvuII. (ER1 or ER2) XhoI.(−120 to TSS BglII).HindIII.[luciferase].XbaI_

Thus, using this strategy at least seven copies of the enhancer regions (ER1, ER2 or ER3, individually or in combination), one at a time, can be added by using one more restriction site upstream of the previous one in PCR amplification of the enhancer regions of choice.

Once the desired number of copies of the enhancer regions are added, AIG is inserted downstream of the superpromoter as described in the STEP 5 of the scheme 1.

The inducible expression of the chimeric TNFp-AIG gene is tested by transient transfection of the cell lines mentioned above. The expression of TNFp-AIG gene is measured by detecting apoptosis of transfected cells, assessing AIG expressed proteins in Western blots using commercially available antibodies and assessing protease activity using commercially available, well documented specific synthetic tetrapeptide substrate.

The inducible expression of the chimeric TNFp-FasL gene is tested by transient transfection of the same cell lines. The cell surface expression of FasL by the transfected cells is quantitated using anti-FasL antibody binding as detected by indirect immunofluorescence and by measuring induction of apoptosis of Fas positive cells.

Regulation of the TNFp-driven expression of a reporter gene. The 3' untranslated region of the TNFα gene plays an important role in reulation of the TNFα biosynthesis. It is involved in translational expression of the TNFα gene in normal, non-activated states. Importantly, these elements allow de-repression to occur when TNFα-producing cells are activated by external stimuli (Han, J., et al., *J. Immunology*, 1991, 146, 1843–1848; Crawford, F. K., et al., *J. Biol. Chem.*, 1996, 271, 22383–22390).

Figure 9:
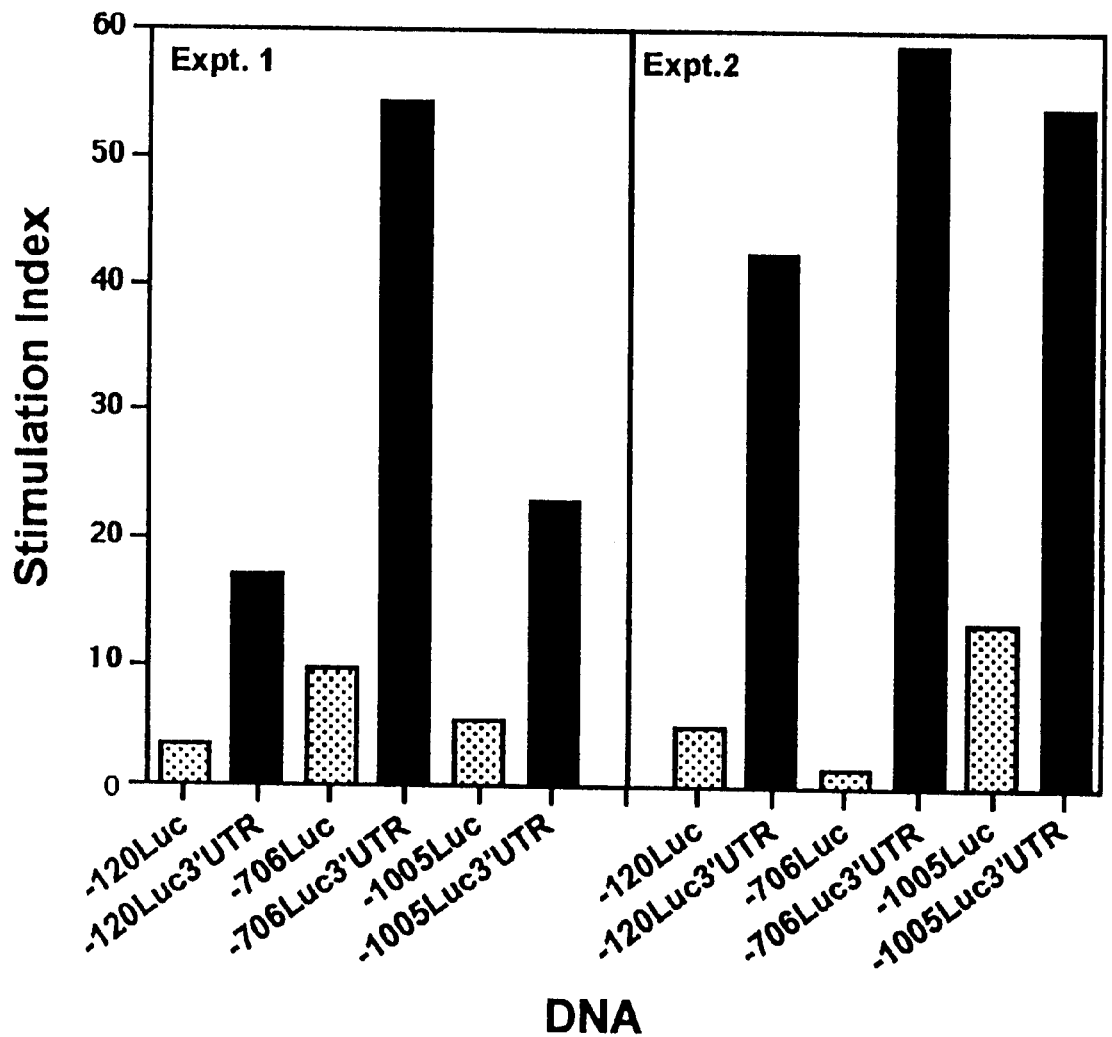
FIG. 9 shows a summary of the results of two experiments to show the regulatory effect of the TNF3'UTR on inducible expression of the luciferase reporter gene. The transient transfection was performed in a fibroblast cell line. Dotted histograms represent inducibility of TNFpLuc in the absence of TNF3'UTR and solid histograms represent inducibility of TNFpLuc in the presence of TNF3'UTR. Similar results are obtained in the Jurkat cell.
Figure 10:
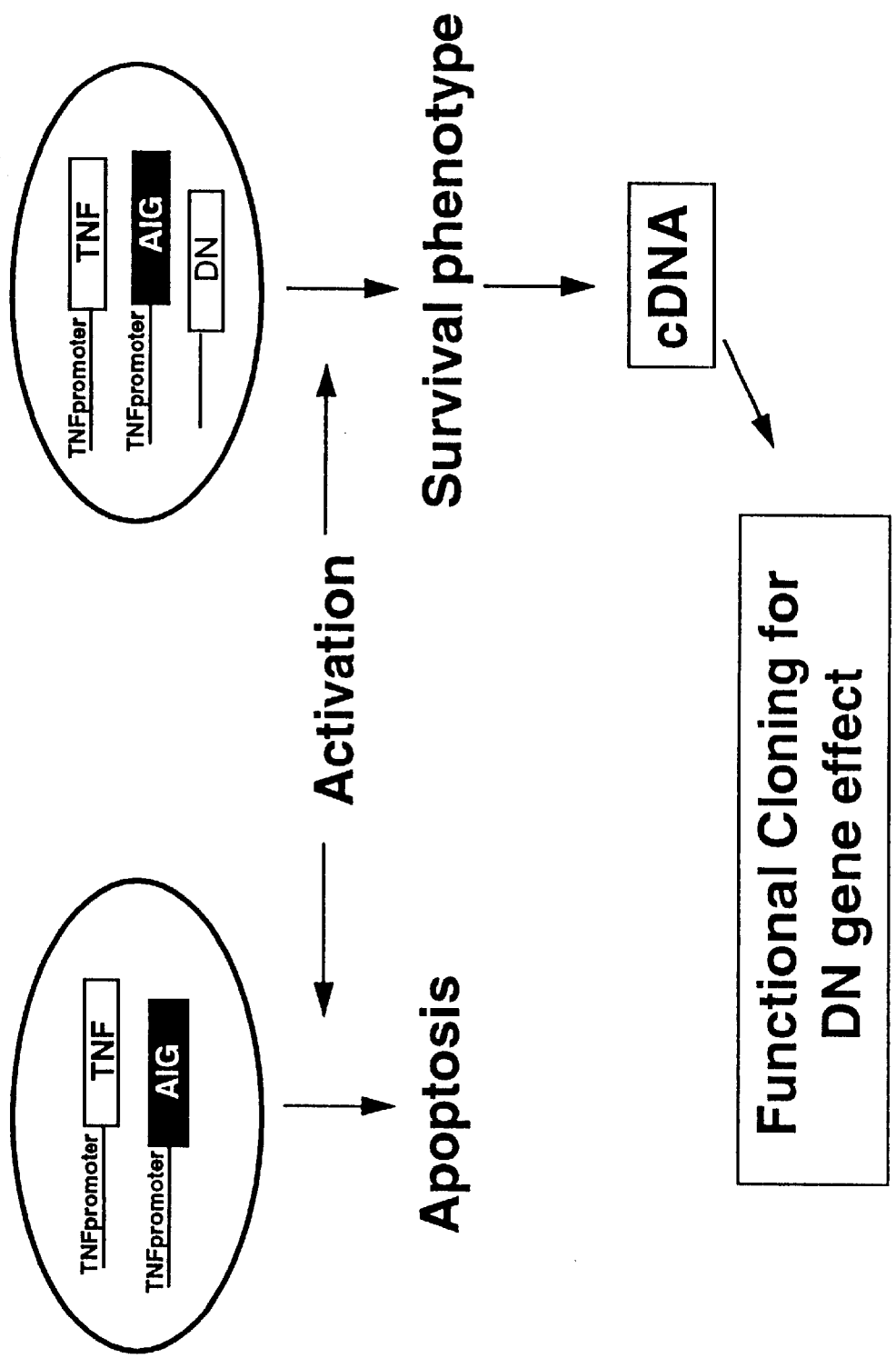
FIG. 10 is a diagrammatic representation for the selection of TNFα non-producer somatic cell variants within a TNFα-producing cell population and identification of dominant negative suppressive genes responsible for inhibiting TNF-α production.

Genetic constructs are made in which the entire 3' untranslated region (SEQ ID NO: 13) is inserted downstream of the luciferase gene driven by deletion fragments, viz., −120, −706 and −1005 of the TNFα promoter. The results of the transient expression of these constructs are summarized in FIG. 9.

Example 2

Testing Protocols

In Vitro Methods

Luciferase assay: Luciferase activity is determined using commercially available reagents (Promega).

AIG.1 and AIG.2 Gene Expression a) Western blots of the transfected cell lysates are developed using anti-CPP32 antibody as well as anti-PRAP antibody. Anti-PRAP antibody detects both hydrolyzed as well as non-hydrolyzed products of PRAP as an enzymatic action of CPP32.

b) CPP32 enzyme assay: This assay detects enzymatic reaction of CPP32 and breakdown of calorimetric or fluorogenic substrate. Commercially available (Clonotech, Pharmingen) kit ise used for this assay.

c) Apoptosis of transfected cells: Apoptosis of transfected cells due to AIG.1 and AIG.2 is determined by staining nuclei by propidium iodide (Krishan, A., J. Cell Biol., 66, 1994, 188–193) and by commercially available Cell Death Elisa kit (Boehringer Mannheim).

Animal Models

Rabbit model of IL-1-induced arthritis (Pettipher E. R., et al., *Proc. Natl. Acad. Sci.*, 1986, 83, 8749–8753): IL-1 is injected into the knee joints of New Zealand White rabbits. Intra-articular injection of IL-1 causes dose-dependent infiltration of leukocytes into the joint space and loss of proteoglycan from the articular cartilage.

Antigen-Induced arthritis: Intra-articular injection of antigen (ovalbumin) into knee joints induces leukocyte accumulation and cartilage degradation that closely resembles rheumatoid arthritis in humans. The joint swelling following the injection was sustained for 14 days.

Scid mice-human synoviocytes model (Houri J. M., et al. *Current Opinions in Rheumatol.*, 1995, 7, 201–205; Sack U., et al., *J. Autoimmunity*, 1995, 9, 51–58; Geiler T., et al. *Arthritis & Rheumatism*, 1994, 37, 1664–1671): These are recently developed models for arthritis in which fresh synovial tissue from RA patients is implanted with normal human cartilage into scid mice either subcutaneously, under the renal capsule (Geiler T., et al., *Arthritis & Rheumatism*, 1994, 37, 1664–1671), or into knee joints (Sack U., et al., *J.*

*Autoimmunity*, 1995, 9, 51–58). The implants grow with arthritis-like characteristics, including formation of pannus tissue of high cellular density, bone and cartilage erosion, development of multinuclear giant cells, and invasion of cartilage by synovial fibroblasts.

Indirect Method: Synoviocytes are transfected in vitro with the therapeutic gene and transplanted back in rabbits. Arthritis is induced in these rabbits by injecting IL-1 and expression of the therapeutic gene following activation is assessed. Activation-induced expression of the chimeric gene induces apoptosis in transplanted cells.

Direct Method: Intra-articular injection of the chimeric genes. Any of the gene delivery methods described above, including naked plasmid DNA, cationic liposome-mediated delivery can be used. For use of viral vector-based delivery, chimeric genes are cloned in suitable vectors. The vectors are then modified by deleting eukaryotic promoter present in these vectors. Intra-articular injection of the therapeutic genes inserted in appropriate vectors can then be done to assess therapeutic as well as prophylactic efficacy.

Example 3

Selection of TNF-α Non-Producer Somatic Cell Variants

Cells (THP-1, Jurkat) are stably transfected in vitro with TNFp-AIG chimeric gene. After several cycles of stimulation, which induces apoptosis in the cells expressing the TNFp-AIG gene, surviving cells are then collected. A cDNA library from these cells is constructed, which is used for functional cloning (Legerski R and Peterson C., *Nature*, 1992, 359, 70–73; Jaattela M., et al., *Oncogene*, 1995, 10, 2297–2305).

Example 4

Identification and Characterization of Dominant Negative (DN) Genes

THP-1 and Jurkat cells stably transfected with TNFp-AIG are subjected to repeated cycles of stimulation to activate expression of TNFp-AIG. The cells, which do not express negative regulatory genes, undergo apoptosis, whereas those expressing dominant negative genes survive. In these surviving cells DN gene products act in-trans with the TNFα promoter, thereby inhibiting its activations to transcribe AIG, ultimately resulting in survival phenotype. cDNA library is constructed using polyadenylated mRNA from these cells. The DN genes which rescue TNFp-AIG-transfected THP-1 or Jurkat cells from apoptosis are identified by functional cloning as described for other genes (Legerski R. and Peterson C., *Nature*, 1992, 359, 70–73; Jaattela M., et al., *Oncogene*, 1995, 10, 2297–2305).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers cited herein are expressly incorporated in their entireties by reference.

What is claimed is:

1. A chimeric gene comprising at least one TNFα enhancer attached to a functional copy of a minimal TNFα promoter and further attached to at least one copy of an apoptosis-inducing gene, wherein the TNFα enhancer is SEQ ID NO: 10 or SEQ ID NO: 11, and wherein the expression of the apoptosis-inducing gene is driven by the TNFα promoter, and wherein the chimeric gene is expressed in inflammatory cells producing TNFα such that self-regulated apoptosis occurs.

2. A chimeric gene comprising at least one TNFα enhancer attached to a functional copy of a minimal TNFα promoter and further attached to at least one copy of an apoptosis-inducing gene, wherein the TNFα is selected from the group consisting of SEQ ID NO: 1, SEQ ID NO: 2, SEQ ID NO: 3, and wherein the expression of the apoptosis-inducing gene is driven by the TNFα promoter, and wherein the chimeric gene is expressed in inflammatory cells producing TNFα such that self-regulated apoptosis occurs.

3. A chimeric gene comprising at least one TNFα enhancer attached to a functional copy of a minimal TNFα promoter and further attached to at least one copy of an apoptosis-inducing gene, wherein the expression of the apoptosis-inducing gene is driven by the TNFα promoter, and wherein the chimeric gene is selected from the group consisting of SEQ ID NO: 4, SEQ ID NO: 5, SEQ ID NO: 6, SEQ ID NO: 7, SEQ ID NO: 8, and SEQ ID NO: 9, and wherein the chimeric gene is expressed in inflammatory cells producing TNFα such that self-regulated apoptosis occurs.

4. The chimeric gene according to claim 3 wherein the 3'UTR of the TNFα gene is ligated downstream of the apoptosis-inducing gene.

* * * * *